United States Patent
Aboul-Hosn et al.

(10) Patent No.: US 6,969,379 B1
(45) Date of Patent: Nov. 29, 2005

(54) INTRAVASCULAR CANNULATION APPARATUS AND METHODS OF USE

(75) Inventors: Walid N Aboul-Hosn, Sacramento, CA (US); William R Kanz, Sacramento, CA (US)

(73) Assignee: A-Med Systems, Inc., W. Sacramento, CA (US)

(*) Notice: Subject to any disclaimer, the term of this patent is extended or adjusted under 35 U.S.C. 154(b) by 0 days.

(21) Appl. No.: 09/763,911

(22) PCT Filed: Aug. 27, 1999

(86) PCT No.: PCT/US99/19537
§ 371 (c)(1),
(2), (4) Date: Feb. 27, 2001

(87) PCT Pub. No.: WO00/12148
PCT Pub. Date: Mar. 9, 2000

Related U.S. Application Data
(60) Provisional application No. 60/098,118, filed on Aug. 27, 1998.

(51) Int. Cl.[7] .......................... A61B 5/28; A61M 31/00; A61M 37/00
(52) U.S. Cl. .................. 604/507; 600/526; 128/898
(58) Field of Search ................ 604/507, 103.7, 604/22; 128/898; 600/309, 529; 606/192

(56) References Cited

U.S. PATENT DOCUMENTS

| | | | |
|---|---|---|---|
| 4,016,884 A | 4/1977 | Kwan-Gett | |
| 4,955,856 A | 9/1990 | Phillips | |
| 5,405,341 A | 4/1995 | Martin | |
| 5,435,308 A | 7/1995 | Gallup et al. | |
| 5,536,242 A | * 7/1996 | Willard et al. | ................ 604/22 |
| 5,695,457 A | 12/1997 | St. Goar et al. | |
| 5,741,234 A | 4/1998 | Aboul-Hosn | |
| 5,769,812 A | 6/1998 | Stevens et al. | |
| 5,814,016 A | 9/1998 | Valley et al. | |
| 5,957,839 A | * 9/1999 | Kruse et al. | ................ 600/309 |

(Continued)

FOREIGN PATENT DOCUMENTS

| | | |
|---|---|---|
| WO | WO 99/02204 | 1/1999 |
| WO | WO 99/59652 | 11/1999 |
| WO | WO 99/65546 | 12/1999 |
| WO | WO 00/12148 | 3/2000 |
| WO | WO 00/18448 | 4/2000 |
| WO | WO 00/19097 | 4/2000 |
| WO | WO 00/37139 | 6/2000 |
| WO | WO 00/69489 | 11/2000 |
| WO | WO 01/17581 | 3/2001 |
| WO | WO 01/54749 | 8/2001 |

Primary Examiner—Nicholas D. Lucchesi
Assistant Examiner—Roz Maiorino
(74) Attorney, Agent, or Firm—Ryan Kromholz & Manion, S.C.

(57) ABSTRACT

This invention is a cannulation apparatus, and related methods for providing indirect access to a surgical site within a patient. The cannulation apparatus includes at least two fluid flow paths that are slidable coupled (40) (50) to one another, and selectively positional within the patient. The first, the second flow path s may be advanced through a single incision disposed remotely from the surgical field to first, and second predetermined locations within the patient. Exemplary sites for the incision include the groin region or in the neck region of the patient. The cannulation apparatus, and method of the present invention are particularly suited for use in providing cardiopulmonary support during cardiac surgery, including coronary artery bypass graft surgery. The cannulation apparatus of the present invention also provides an entry site for one or more support devices used in the surgical procedure.

4 Claims, 21 Drawing Sheets

U.S. PATENT DOCUMENTS

| | | | |
|---|---|---|---|
| 5,971,973 A | * 10/1999 | Peters | 604/101.05 |
| 6,033,401 A | * 3/2000 | Edwards et al. | 606/41 |
| 6,083,260 A | 7/2000 | Aboul-Hosn | |
| 6,086,570 A | 7/2000 | Aboul-Hosn et al. | |
| 6,113,536 A | 9/2000 | Aboul-Hosn et al. | |
| 6,123,725 A | 9/2000 | Aboul-Hosn | |
| 6,152,704 A | 11/2000 | Aboul-Hosn et al. | |
| 6,210,133 B1 | 4/2001 | Aboul-Hosn et al. | |
| 6,210,397 B1 | 4/2001 | Aboul-Hosn et al. | |
| 6,228,063 B1 | 5/2001 | Aboul-Hosn | |
| 6,234,960 B1 | 5/2001 | Aboul-Hosn et al. | |
| 6,287,319 B1 | 9/2001 | Aboul-Hosn et al. | |
| 6,293,920 B1 | 9/2001 | Sweezer et al. | |
| 6,295,877 B1 | 10/2001 | Aboul-Hosn et al. | |
| 6,395,026 B1 | 5/2002 | Aboul-Hosn et al. | |
| 6,508,777 B1 | * 1/2003 | Macoviak et al. | 604/4.01 |

* cited by examiner

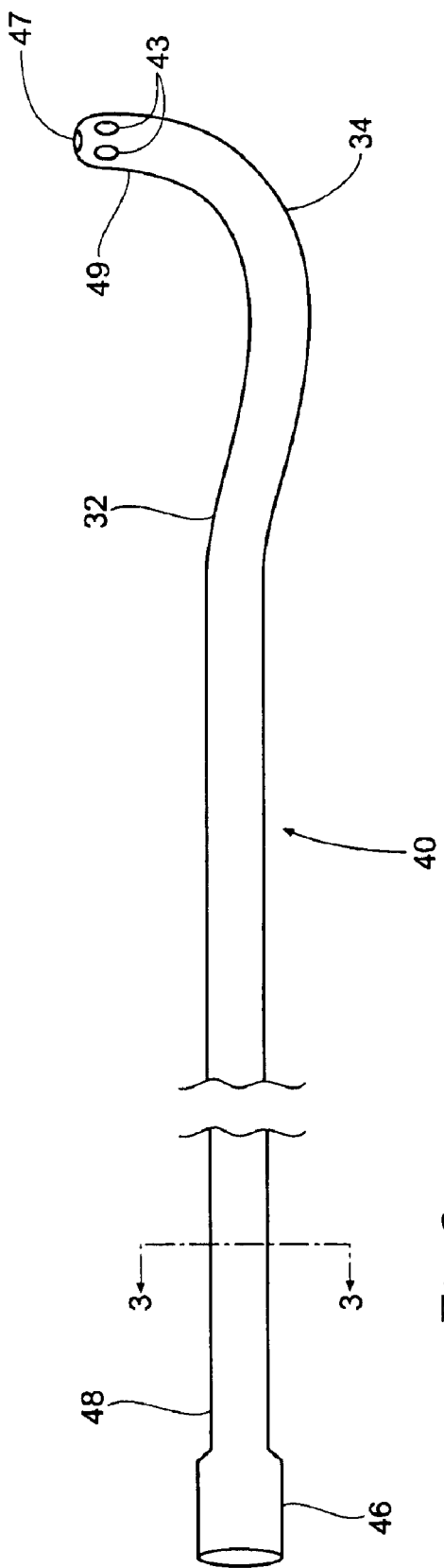
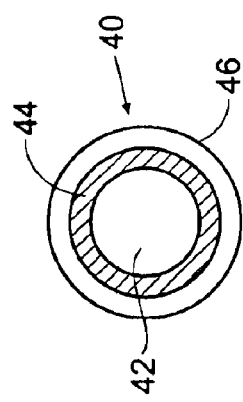
Fig. 2
Fig. 3

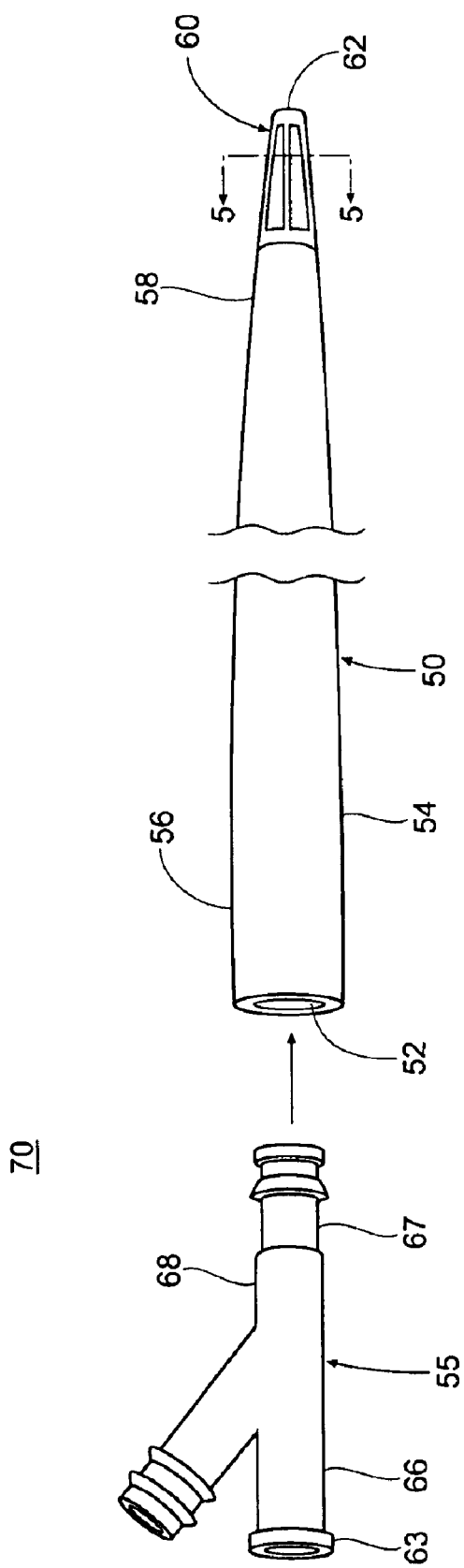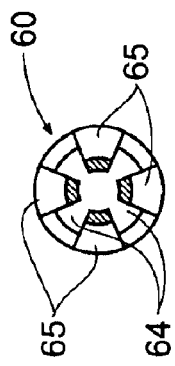
Fig. 4
Fig. 5

Fig. 28A
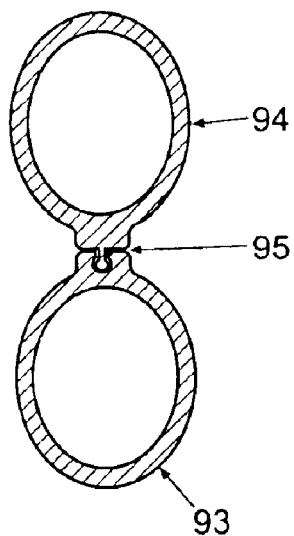
Fig. 28C
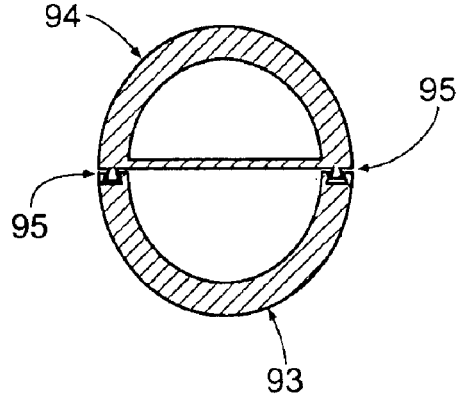
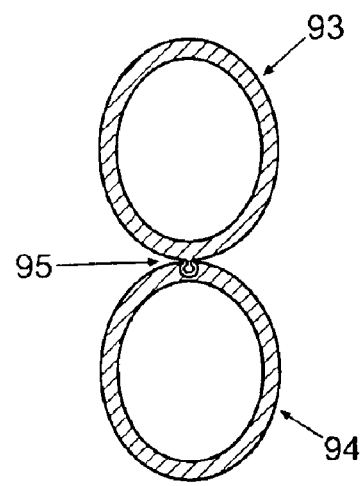
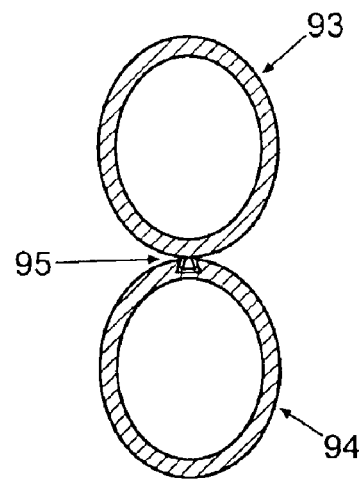
Fig. 28B
Fig. 28D

INTRAVASCULAR CANNULATION APPARATUS AND METHODS OF USE

CROSS-REFERENCE TO RELATED APPLICATIONS

This application claims the benefit under Title 35, United States Code, §119(e) of U.S. Provisional Application No. 60/098,118 filed on Aug. 27, 1998 entitled "Intravascular Cannulation Apparatus and Method of Use."

BACKGROUND OF THE INVENTION

1. Field of the Invention

The present invention relates generally to methods and devices for cannulation and, more particularly, to an intravascular cannulation assembly having at least two flow paths slidably coupled to one another suitable for use in a variety of cardiac procedures.

2. Description of Related Art

Cannulas and cannulation techniques are used in medical applications for transporting fluid into or out of the body. An area of proliferated use is cardiac surgery, where cannulation is routinely employed to transport fluid into, out of, or between various points in the circulatory system. This may be done for the purpose of performing cardiac procedures including, but not limited to, cardiopulmonary bypass (CPB), as well as left-heart and/or right-heart assist procedures.

The role of cannulation in cardiac surgery may be described by way of example with reference to coronary artery bypass graft (CABG) surgery. CABG surgery involves connecting a source of arterial blood downstream from a narrow or occluded section of a coronary artery for the purpose of providing an improved supply of oxygenated blood to the vasculature of the heart. The source of blood is often an internal artery, and the target is typically among the anterior or posterior coronary arteries. CABG surgery may be either open chest or closed chest (minimally invasive). Open chest CABG involves performing a sternotomy to spread the chest apart and provide access to the heart. Closed chest CABG surgery involves accessing the heart through conduits extending into the chest cavity, such as by thoracotomy. CABG surgery may also be performed on a stopped heart or a beating heart.

During stopped heart and beating heart CABG surgery, it is necessary to provide additional circulatory support in order to maintain the hemodynamic stability of the patient. For stopped heart CABG surgery, this is accomplished by establishing full cardiopulmonary bypass (CPB), wherein blood is diverted from the lungs for artificial oxygenation at a remote location. This may be referred to as providing "full" cardiac support. For beating heart CABG surgery, this is preferably accomplished by providing right-heart and/or left-heart assistance, wherein blood is rerouted from one location in the heart to another under the direction of a blood pump so as to obviate the need for an artificial oxygenator, filter, tubing, saline, etc. This may be referred to as providing "partial" cardiac support. Rerouting the blood during beating heart surgery may also serve to unload a selected chamber of the heart in an effort to stabilize the tissue and thus make it easier for the physician to perform the grafting procedure.

The process of placing a patient on full or partial cardiac support is conventionally accomplished using two cannulas. In stopped heart CABG surgery, the first cannula is placed in the right atrium as an inflow or suction cannula, while the second cannula is placed in the aorta as an outflow or return cannula from the oxygenator. In beating heart CABG surgery, the first cannula may be placed in the right or left atrium, and the second cannula placed within the aorta or pulmonary artery depending upon what side of the heart is being assisted. In either case, placement of the cannulas may be direct or indirect. Direct cannulation involves introducing the cannula directly into the desired heart chamber or major vessel extending directly from the heart (i.e. aorta or pulmonary artery). Indirect cannulation involves advancing the cannula intravascularly into the desired heart chamber or major vessel extending directly from the heart (i.e. aorta or pulmonary artery).

Direct cannulation systems of the prior art suffer a variety of drawbacks. A first drawback is that cannulation can only be performed so long as the chest cavity is maintained open. Another drawback is that introducing the cannulas and related tubing through the chest cavity reduces the field of surgery, that is, the amount of space within which the surgeon has to operate. In addition to reducing the field of surgery, the surgeon must make separate incisions for each cannula, with each incision presenting a potential site for leakage and infection. Direct cannulation through the chest cavity also lengthens the overall time required to perform a CABG procedure because the surgeon must personally position each cannula after opening up the chest cavity. This increases the overall time that the patient's chest will be open and exposed to atmosphere. It is also more costly and ties up valuable hospital resources (i.e. beds, staff, etc . . . ) for a longer period, which can be especially troubling in emergency room situations where a limited number of beds and staff are commonplace.

Indirect cannulation overcomes many of the above-enumerated drawbacks associated with direct cannulation. Indirect cannulation advantageously provides the ability to perform closed chest cardiac surgery in that a sternotomy is not required to access the heart. Indirect cannulation can also be maintained well after the given cardiac procedure is completed. This is advantageous in providing continued circulatory support after a procedure has been completed, as well as providing the ability to close the chest following open chest surgery without jeopardizing cannulation. Indirect cannulation also reduces the clutter from the field of surgery so as to avail more space for the surgeon. It provides the ability to have someone other than the physician establish cannulation. In so doing, indirect cannulation allows the doctor to perform the cardiac procedure in the least amount of time, thereby reducing cost.

While indirect cannulation presents significant improvements over direct cannulation, the prior art indirect cannulation systems are nonetheless flawed. One disadvantage of prior art indirect cannulation systems is that the cannulas are rigidly fixed to one another and thereby do not provide any degree of adjustability between the distal ends of the cannulas. This severely restricts the ability to place a particular cannula assembly in the appropriate locations in the circulatory system. In so doing, it will result in much guess-work in selecting a cannulation assembly of the appropriate size. Inefficiency in selecting and placing an appropriately sized cannulation assembly translates into increased costs, both in terms of hospital resources (i.e. beds, staff, etc . . . ) as well as the unnecessary costs associated with discarding cannulation assemblies that were introduced into the circulatory system and later found out to be inappropriately sized for the intended cardiac support function. Prior art indirect cannulation systems are also limited in terms of their flow characteristics.

The present invention is directed at eliminating and/or reducing the effects of the foregoing drawbacks of prior art.

SUMMARY OF THE INVENTION

One aspect of the present invention involves a cannulation assembly for providing circulatory support. The cannulation assembly comprises a first flow path for transporting blood between a pump and a first predetermined location within the circulatory system of a patient. A second flow path is provided for transporting blood between a pump and a second predetermined location within the circulatory system of a patient. The first and second flow paths are slidably coupled to one another and dimensioned to extend, in use, into the respective first and second predetermined locations through a single incision formed in the vascular system of the patient.

In one embodiment of the cannulation assembly, the first and second flow paths are disposed in a generally coaxial arrangement with the second flow path disposed at least partially within the first flow path.

In one embodiment of the cannulation assembly, the first and second flow paths are coupled together in a generally side-by-side arrangement.

In one embodiment of the cannulation assembly, at least one of the first and second flow paths is equipped with an auxiliary lumen.

In one embodiment of the cannulation assembly, the auxiliary lumen is sized to receive at least one of a guide wire, a pressure sensor, and an optical instrument.

In one embodiment of the cannulation assembly, at least one of the first and second flow paths is equipped with an expandable guiding structure.

In one embodiment of the cannulation assembly, the first flow path intakes blood to the pump and the second flow path outputs blood from the pump.

In one embodiment of the cannulation assembly, the first flow path outputs blood from the pump and the second flow path intakes blood to the pump.

In one embodiment of the cannulation assembly, at least one of the first and second flow paths is equipped with at least one of a flow rate sensor, a pressure sensor, and an optical sensor.

In one embodiment of the cannulation assembly, at least one of the first and second flow paths is equipped with an auxiliary fluid flow lumen.

In one embodiment of the cannulation assembly, at least one of the first and second flow paths is equipped with a bend for directing the flow path to the respective first or second predetermined location in the circulatory system.

In one embodiment of the cannulation assembly, at least one of the first and second flow paths includes a section of material capable of being selectively deformed to create a bend in the flow path to facilitate guiding the flow path into the respective first or second predetermined location in the circulatory system.

In one embodiment of the cannulation assembly, at least one of the first and second flow paths is equipped with a plurality of apertures for facilitating fluid flow into or out of the respective first or second flow paths.

In one embodiment of the cannulation assembly, the first flow path includes a plurality of drainage apertures to facilitate fluid flow through the first flow path.

In one embodiment of the cannulation assembly, the second flow path includes a narrow region that, in use, is disposed approximately adjacent to the drainage apertures of the first flow path.

In one embodiment of the cannulation assembly, the second flow path includes a wide region that, in use, is disposed approximately adjacent to the drainage apertures of the first flow path.

In another aspect of the present invention, a cannulation assembly is provided comprising a first flow path slidably coupled to a second flow path such that the first and second flow paths may be introduced into the vascular system of a patient through a single incision and positioned at respective first and second predetermined locations within the circulatory system of the patient.

In one embodiment of the cannulation assembly, at least one of the first and second flow paths is independently positionable relative to the incision after being inserted into the vascular system of the patient.

In one embodiment of the cannulation assembly, at least one of the first and second flow paths is the distance between a distal end of the first flow path and the distal end of the second flow path may be selectively adjusted by selectively sliding one of the first and second flow paths relative to the other.

In one embodiment of the cannulation assembly, the first and second flow paths are configured such that, in use, the distal end of the second flow path will be located a fixed distance from the distal end of the first flow path.

In one embodiment of the cannulation assembly, the first and second flow paths are disposed in a generally coaxial arrangement with the second flow path disposed at least partially within the first flow path.

In one embodiment of the cannulation assembly, the first and second flow paths are coupled together in a generally side-by-side arrangement.

In one embodiment of the cannulation assembly, at least one of the first and second flow paths is equipped with an auxiliary lumen.

In one embodiment of the cannulation assembly, the auxiliary lumen is sized to receive at least one of a guide wire, a pressure sensor, and an optical instrument.

In one embodiment of the cannulation assembly, at least one of the first and second flow paths is equipped with an expandable guiding structure.

In one embodiment of the cannulation assembly, the first flow path intakes blood to the pump and the second flow path outputs blood from the pump.

In one embodiment of the cannulation assembly, the first flow path outputs blood from the pump and the second flow path intakes blood to the pump.

In one embodiment of the cannulation assembly, at least one of the first and second flow paths is equipped with at least one of a flow rate sensor, a pressure sensor, and an optical sensor.

In one embodiment of the cannulation assembly, at least one of the first and second flow paths is equipped with an auxiliary fluid flow lumen.

In one embodiment of the cannulation assembly, at least one of the first and second flow paths is equipped with a bend for directing the flow path to the respective first or second predetermined location in the vascular system.

In one embodiment of the cannulation assembly, at least one of the first and second flow paths includes a section of material capable of being selectively deformed to create a bend in the flow path to facilitate guiding the flow path into the respective first or second predetermined location in the vascular system.

In one embodiment of the cannulation assembly, at least one of the first and second flow paths is equipped with a plurality of apertures for facilitating fluid flow into or out of the respective first or second flow paths.

In one embodiment of the cannulation assembly, the first flow path includes a plurality of drainage apertures to facilitate fluid flow through the first flow path.

In one embodiment of the cannulation assembly, the second flow path includes a narrow region that, in use, is disposed approximately adjacent to the drainage apertures of the first flow path.

In one embodiment of the cannulation assembly, the second flow path includes a wide region that, in use, is disposed approximately adjacent to the drainage apertures of the first flow path.

A still further aspect of the present provides a method for providing circulatory support. The first step involves withdrawing blood from a first predetermined location in the circulatory system of a patient. The second step involves returning the withdrawn blood to a second predetermined location in the circulatory system of the patient. The steps of withdrawing and returning are performed by providing a cannula having a first flow path slidably coupled to a second flow path, wherein the first and second flow paths are dimensioned to extend, in use, respectively into the first and second predetermined locations through a single incision formed in the vascular system of the patient.

In one embodiment of the circulatory support method, the incision is formed in one of the aorta, carotid artery, femoral artery, radial artery, axillary artery, interior jugular vein, external jugular vein, inferior vena cava, superior vena cava, brachiocephalic vein, radial vein, pulmonary artery, and pulmonary vein.

In one embodiment of the circulatory support method, the incision is formed at one of a location between the aorta and carotid artery, the aorta and the femoral artery, the aorta and the radial artery, the aorta and the axiallary artery, the inferior vena cava and the femoral vein, the superior vena cava and the interior jugular vein, and the superior vena cava and the brachiocephalic vein.

In one embodiment of the circulatory support method, the first and second predetermined locations comprise respectively the right atrium and the pulmonary vein.

In one embodiment of the circulatory support method, the first and second predetermined locations comprise respectively the left ventricle and the aorta of the patient.

In one embodiment of the circulatory support method, the second flow path is coaxial with and extends at least partially within the first flow path.

In one embodiment of the circulatory support method, the first and second flow paths are coupled together in a generally side-by-side arrangement.

In one embodiment of the circulatory support method, the first flow oath is advanced to the first predetermined location using the Seldinger technique.

In one embodiment of the circulatory support method, the second flow path is advanced to the second predetermined location using a guiding device.

In one embodiment of the circulatory support method, the second flow path is advanced to the second predetermined location using a flow directed guiding device.

In one embodiment of the circulatory support method, the guiding device comprises a guide wire supported within a dedicated auxiliary lumen formed in the second flow path.

In one embodiment of the circulatory support method, at least one of the first and second flow paths is advanced using the cut down technique.

Yet another aspect of the present invention provides a method for inserting a cannula assembly into a patient. The method comprises the steps of: (1) forming a single incision in the vascular system of the patient; (2) providing a cannula assembly having a first flow path slidably coupled to a second flow path; (3) advancing a distal end of the first flow path through the incision to a first predetermined location within the circulatory system of the patient; and (4) advancing a distal end of the second flow path through the incision to a second predetermined location within the circulatory system of the patient.

In one embodiment of the cannula assembly insertion method, the incision is formed in one of the aorta, carotid artery, femoral artery, radial artery, axillary artery, interior jugular vein, external jugular vein, inferior vena cava, superior vena cava, brachiocephalic vein, radial vein, pulmonary artery, and pulmonary vein.

In one embodiment of the cannula assembly insertion method, the incision is formed at one of a location between the aorta and carotid artery, the aorta and the femoral artery, the aorta and the radial artery, the aorta and the axiallary artery, the inferior vena cava and the femoral vein, the superior vena cava and the interior jugular vein, and the superior vena cava and the brachiocephalic vein.

In one embodiment of the cannula assembly insertion method, the first and second predetermined locations comprise respectively the right atrium and the pulmonary vein.

In one embodiment of the cannula assembly insertion method, the first and second predetermined locations comprise respectively the left ventricle and the aorta of the patient.

In one embodiment of the cannula assembly insertion method, the second flow path is coaxial with and extends at least partially within the first flow path.

In one embodiment of the cannula assembly insertion method, the first and second flow paths are coupled together in a generally side-by-side arrangement.

In one embodiment of the cannula assembly insertion method, the first flow path is advanced to the first predetermined location using the Seldinger technique.

In one embodiment of the cannula assembly insertion method, the second flow path is advanced to the second predetermined location using a guiding device.

In one embodiment of the cannula assembly insertion method, the second flow path is advanced to the second predetermined location using a flow directed guiding device.

In one embodiment of the cannula assembly insertion method, the guiding device comprises a guide wire supported within a dedicated auxiliary lumen formed in the second flow path.

In one embodiment of the cannula assembly insertion method, at least one of the first and second flow paths is advanced using the cut down technique.

A still further aspect of the present invention provides a method for providing circulatory support. The method comprises the steps of: (1) providing a first flow path slidably coupled to a second flow path; (2) advancing a distal tip of the first flow path through an incision formed in the vascular system of a patient to a first predetermined location in the circulatory system of a patient; (3) advancing a distal tip of the second flow path through the incision to a second predetermined location in the circulatory system of the patient; (4) withdrawing blood from the first predetermined location in the circulatory system of the patient; and (5) returning the withdrawn blood to the second predetermined location in the circulatory system of the patient.

In one embodiment of the circulatory support method, the incision is formed in one of the aorta, carotid artery, femoral artery, radial artery, axillary artery, interior jugular vein, external jugular vein, inferior vena cava, superior vena cava, brachiocephalic vein, radial vein, pulmonary artery, and pulmonary vein.

In one embodiment of the circulatory support method, the incision is formed at one of a location between the aorta and carotid artery, the aorta and the femoral artery, the aorta and the radial artery, the aorta and the axiallary artery, the inferior vena cava and the femoral vein, the superior vena cava and the interior jugular vein, and the superior vena cava and the brachiocephalic vein.

In one embodiment of the circulatory support method, the first and second predetermined locations comprise respectively the right atrium and the pulmonary vein.

In one embodiment of the circulatory support method, the first and second predetermined locations comprise respectively the left ventricle and the aorta of the patient.

In one embodiment of the circulatory support method, the second flow path is coaxial with and extends at least partially within the first flow path.

In one embodiment of the circulatory support method, the first and second flow paths are coupled together in a generally side-by-side arrangement.

In one embodiment of the circulatory support method, the first flow path is advanced to the first predetermined location using the Seldinger technique.

In one embodiment of the circulatory support method, the second flow path is advanced to the second predetermined location using a guiding device.

In one embodiment of the circulatory support method, the second flow path is advanced to the second predetermined location using a flow directed guiding device.

In one embodiment of the circulatory support method, the guiding device comprises a guide wire supported within a dedicated auxiliary lumen formed in the second flow path.

In one embodiment of the circulatory support method, at least one of the first and second flow paths is advanced using the cut down technique.

Another aspect of the present invention provides a method of circulating fluid through a cannula system comprising a cannulation assembly including at least two flow paths slidably coupled to each other. The method comprises the steps of: (1) inserting the cannulation assembly into a first predetermined location in a body through a vascular incision; (2) establishing flow communication between a first one of the flow paths and the first predetermined location; (3) slidably moving a second one of the flow paths into a second predetermined location spaced apart from the first predetermined location; (4) establishing flow communication between the second flow path and the second predetermined location; (5) coupling the first and second flow paths to a pump system; and (6) operating the pump system to transport fluid from the first predetermined location for introduction into the second predetermined location.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 2 is schematic view of an inner cannula of the cannulation assembly of the present invention;

FIG. 3 is a cross-sectional view taken along line 3—3 in FIG. 2;

FIG. 4 is a schematic view of an outer cannula and connector of the cannulation assembly of the present invention;

FIG. 5 is a cross sectional view taken along line 5—5 in FIG. 4;

FIGS. 28A–28D are cross-sectional views taken along line 28—28 in FIG. 27 illustrating exemplary coupling mechanisms suitable for slidably coupling the first and second cannulas in accordance with the present invention;

DETAILED DESCRIPTION OF THE INVENTION

The present invention involves a cannulation assembly for use in any of a number of broad ranging applications involving the introduction and/or removal of fluids into and/or from the body. The cannulation assembly of the present invention is particularly suited for use in cardiac applications, although it is to be readily understood that the cannulation assembly and methods of the present invention are not to be limited to cardiac applications. By way of example only, the cannulation assembly of the present invention is useful in certain cardiac application, including, but not limited to, procedures involving coronary bypass graft (CABG), cardiopulmonary bypass (CPB), left-heart and/or right-heart assist, open chest and closed chest (minimally invasive), cannulation of a vessel, bridge-to-transplant and/or failure-to-weanfrom-bypass.

The term "cannula" as used herein is to be defined as a hollow (although not necessarily tubular) instrument designed to be introduced into a body cavity for the purpose of transporting fluid into or out of the body cavity. The term "catheter" as used herein is to be defined as a slender flexible tube of minimal diameter that can be inserted into a bodily channel, such as a vein, for guiding and/or sensing purposes.

The term "vascular system" as used herein is to be defined as the network of arteries and veins in the body with the exception of the heart and major vessels extending directly therefrom. The term "circulatory system" as used herein is to be defined as the entire network of arteries and veins in the body, including the heart and major vessels extending directly therefrom. The term "incision" as used herein is to be construed as any hole, opening, or aperture formed in a vessel or body.

Figure 1:
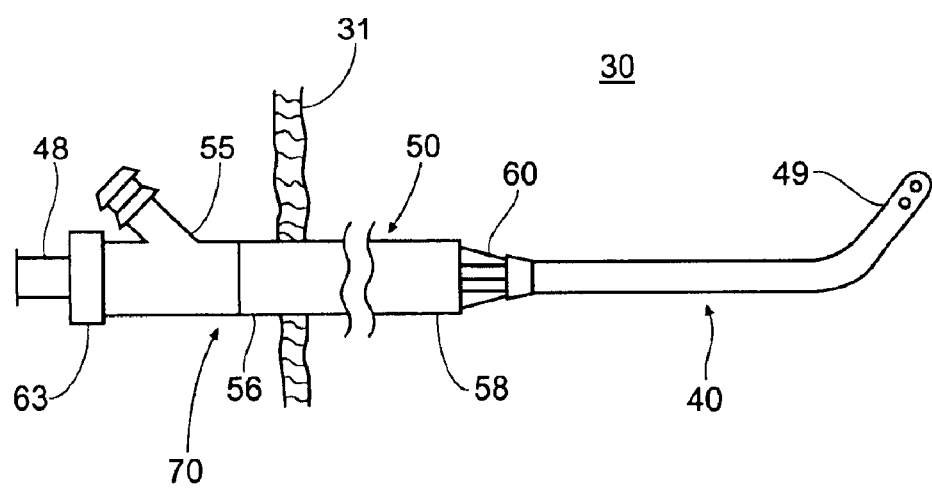
FIG. 1 schematic view of a cannulation assembly in accordance with the invention.

FIG. 1 illustrates an exemplary embodiment of a cannulation assembly 30 of the present invention. Cannulation assembly 30 includes an inner cannula 40 and an outer cannula 50. The proximal ends of inner cannula 40 and outer cannula 50 remain outside the patient's body 31 during use. Inner and outer cannulas 40, 50 may be connected to a pumping system (not shown) used for augmenting blood flow during beating heart surgery. One exemplarly pump is a reverse flow pump of the type described in the commonly assigned, co-pending PCT Application No. PCT/US97/18674, the contents of which are hereby incorporated by reference. A major advantage of such an arrangement is the placement of the pump system and attendant connections, sensors, and other equipment out of the immediate vicinity of the beating heart surgical procedure, freeing up space in which the surgeon can operate. Other advantages include a low priming volume requirement as the pump system can be located closer to the patient's body (i.e. near the patient's neck region) since that region is not being operated on. Additionally, the insertion procedure for the cannulation assembly can be performed prior to the surgical operation, by someone other than the surgeon, such as the anesthesiologist, thereby reducing the length of time required for the heart surgery itself.

The cannulation assembly 30 can be adapted for use in various applications in which fluids are introduced and removed from the body. For purposes of more clearly describing the present invention, the cannulation assembly 30 will be described in terms of use in providing right heart support through the internal jugular vein. However, it is to be understood that the assembly 30 can be configured and adapted by, for example, increasing or decreasing the cannula size and/or number such that the assembly 30 can be beneficially used for other medical applications in which fluids are introduced and removed from the body. More specifically, the device of the present invention may be utilized to provide circulatory support through indirect or remote access of the patient's circulatory system. As used herein, the terms "indirect access" or "remote access" refers to accessing the patient through an incision formed in the patient's vascular system. Indirect or remote access is differentiated from direct access in that direct access typically involves a sternotomy in order to access the patient's circulatory system. Exemplary points for indirectly accessing the patient in accordance with the present invention include, but are not necessarily limited to, the brachiocephalic vein, carotid artery, axillary artery, and femoral vein.

In FIG. 1, the cannulation assembly 30 of the present invention is shown an assembled configuration. The outer cannula 50, which forms part of an outer cannula assembly 70, is dimensioned to receive the inner cannula 40 through an interior lumen (not shown). In the embodiment shown, a y-connector 55 is provided for sealingly mating with the outer cannula 50 to form an outer cannula assembly 70. It is to be readily appreciated that the connector 55 is presented by way of example only and that the cannulation assembly 30 of the present invention is not dependent upon a particular type of connector. During operation, distal end 58 of outer cannula 50 and distal end 49 of inner cannula 40 lie in the patient's body, penetrating through an incision in the patient's tissue 31. In one embodiment, the distal end 58 of outer cannula 50 serves to withdraw blood and the distal end 49 of inner cannula 40 serves to reintroduce the blood into the body. Proximal end 48 of inner cannula 40 and proximal end 56 of outer cannula 50 protrude out of the patient's body and interface with surgical equipment such as a reverse flow pump system (not shown) for augmenting the blood flow as discussed above.

As seen in FIGS. 2 and 3, inner cannula 40 comprises a substantially tubular structure having a wall 44 defining a main lumen 42. The length of the cannula 40 is application specific and depends for example on the size of the patient and the distance from the incision in the neck to the destination in the patient's pulmonary system. In a CPB application, the pulmonary artery is the destination into which blood is returned into the patient from the pump system via inner cannula 40, and the dimensions of inner cannula 40 are selected accordingly.

Inner cannula 40 is provided at its proximal end 48 with a connector 46, which is suitably sized to interface with various surgical instruments (not shown), such as the output (or intake, in some applications) portions of a reverse flow pump (not shown). Inner cannula 40 may be provided with one or more holes 43 disposed at distal end 49, in addition to the open tip 47 of its substantially cylindrical structure, in order to permit more efficient fluid passage. Further, distal tip 49 of inner cannula 40 is tapered to allow insertion into the internal jugular vein.

FIGS. 4 and 5 show the details of outer cannula assembly 70, which generally comprises an outer cannula 50 mated with a y-connector 55. Outer cannula 50 has a main lumen 52 defined by a substantially tubular wall 54. Main lumen 52 extends longitudinally between the proximal end 56 and distal end 58 of the outer cannula 50. Again the length of the cannula 50 and main lumen 52 are selected depending on the size of the patient and other factors as discussed above. Tubular walls 44 and 54 of cannulas 40 and 50 can be formed of materials ranging from rigid to flexible, and in the preferred embodiment comprise a semi-rigid transparent material such as polyurethane or silicone having a hardness of between about 30A and 90A on a Shore durometer scale and capable of withstanding sterilization by ethylene oxide (ETO). Rigid clear materials can be used for the y-connector 55, and preferably y-connector 55 is constructed of polycarbonate or polyvinyl chloride. The cannulas 40 and 50 may also contain radiopaque markings (not shown) to determine placement within the patient's body. To provide structural reinforcement, a spiraling wire (not shown) can be provided for support of the walls 44 and 54. The spiraling wire (not shown) may be molded into the walls or is otherwise supported therein, and may extend either partially or fully across the length of the cannulas 40 and 50. The wire facilitates handling of the cannulas and reduces the possibility of the cannulas' collapsing or being pinched shut and thus closing off the flow of fluid to or from the patient. Other ways of reinforcing the tubular bodies of the cannulas 40 and 50 are known in the art and will adapt equally well to the present invention. In addition, no reinforcement may be needed if the cannula material is sufficiently rigid or if sufficient fluid flow is present within the cannulas.

Figure 6:
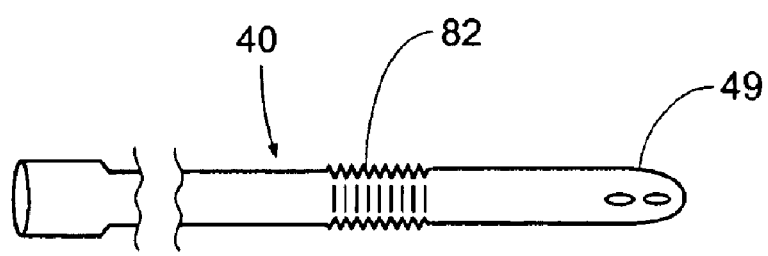
FIG. 6 is a schematic view of an inner cannula having a joint formed of current responsive material in accordance with the present invention.
Figure 7:
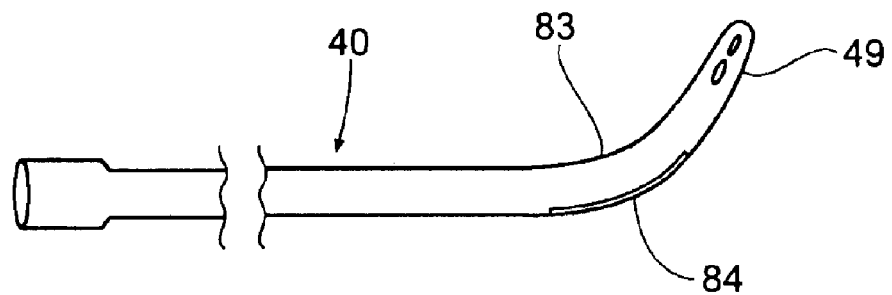
FIG. 7 is a schematic view of a cannula having a controllable preformed curve in accordance with the present invention.

One or more pre-formed curves may be provided in the inner cannula 40 and/or the outer cannula 50. Referring briefly to FIG. 2, the preformed curves, designated as 32 and 34 in inner cannula 40, facilitate cannula maneuverability during insertion in the patient's body, permitting the negotiation of tortuous passages such as through the atria, ventricular valve and pulmonary valve. The angle of the preformed curves may be anywhere in the range of 0–180°, with the curves being disposed anywhere along the length of the cannulas 40,50 and in any one or more distinct planes, depending on the particular application. The curves may also be of an adjustable angle, formed by expandable joints. In one such construction, illustrated in FIG. 6, the inner cannula 40 may be provided with expandable joint 82 for changing the length and/or orientation of distal end 49 with respect to the body of inner cannula 40 by passing a current through or eliminating a current through joint 82. Joint 82 is constructed of a memory shaped material which, in the presence of current, will either change length or shape depending upon the characteristics of material used. An example of such a material for use in joint 82 is Nitinol™, commercially available from Educational Innovations, Inc. 151 River Road, Cos Cab Conn. 06807. As illustrated in FIG. 7, distal end 49 of cannula 40 may be initially bent as shown, whereby a strip 84 of Nitinol™ is placed within the tubular wall of cannula 40 and initially shaped to form curvature 83 in cannula 40. Curvature 83 may be selectively changed by passing a current within the Nitinol™ wire 84, thereby allowing the operator to change the position and orientation of distal end 49. In another construction of an adjustable lumen, cables may be provided which serve to impart or relieve forces inducing deformation and curvature of the cannula.

Referring once again to FIGS. 4 and 5, attached at distal end 58 of outer cannula 50 is tip 60 formed of a biocompatible, preferably polymeric, material adapted to rigidly retain the inner cannula 40 in position within outer cannula 50. The diameter of lumen 52 is selected to be larger than the outer diameter of inner cannula 40 to thereby permit fluid passage through main lumen 52 in the presence of inner cannula 40 in main lumen 52. Tip 60 is preferably of a more rigid construction than the material of tubular wall 54 to provide better support for cannula 40 and for insertion into the body. In addition to a main channel 62 for passage of inner cannula 40, tip 60 is also provided with peripheral holes 64 for efflux of fluid to or from outer cannula 50. Peripheral holes 64 are formed between supports 65 extending substantially longitudinally along tip 60, preferably having a tapered shape with a decreasing diameter in the direction of the distal end of tip 60. The combined area of the holes 64 is greater than the sectional area between the inner cannula 40 and outer cannula 50, thereby allowing partial blockage of holes 64 without loss of flow through tip 60 or outer cannula 50.

Y-Connector 55 provides a means for interfacing the inflow and outflow portions of the pump system (not shown) with the cannulas 40 and 50. It is to be understood that other types of connectors can be used to effect this interface. Additionally, the range of different types of pumps with which the invention can be practiced is broad because of the reduced priming volume and the novel arrangement of the cannulas with respect to the patient. Examples of possible pumps include, but are not limited to, co-axial reverse flow pumps, roller pumps, and centrifugal pumps.

Figure 8:
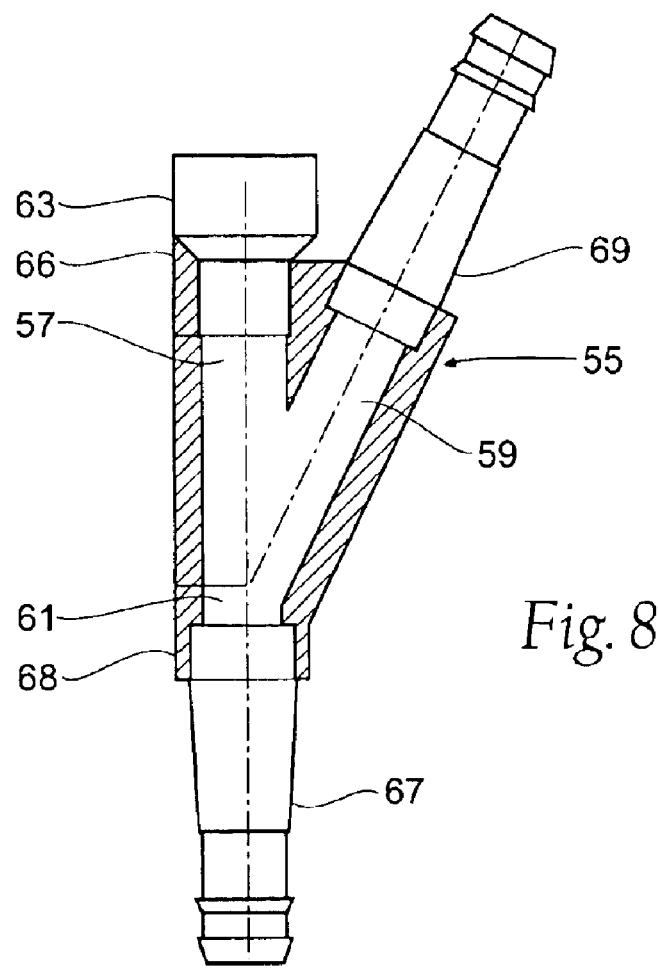
FIG. 8 is a cut-away view of a y-connector in accordance with the invention.
Figure 9:
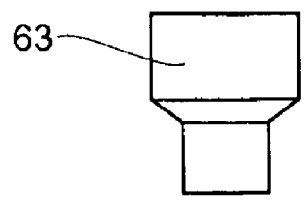
FIG. 9 is a schematic view of a hemostasis valve in accordance with the invention.

As shown in more detail in FIG. 8, y-connector 55 comprises first channel 57 and second channel 59, defined by substantially tubular walls, which converge into main channel 61 extending co-axially with first channel 57. Hemostasis valve 63 (FIG. 9) is provided at proximal end 66 of y-connector 55 and serves to form a seal around for example inner cannula 40 once inner cannula 40 is fitted therethrough. A fitting 67 is provided at distal end 68 of y-connector 55, fitting 67 adapted to mate with proximal end 56 of outer cannula 50 to form a fluid-tight seal therewith. Additionally, a fitting 69 is provided at channel 59 to facilitate mating with other cannulas or similar apparatus (not shown) such as PVC tubing adapted to receive an ultrasonic flow meter like that used in the Transonic T110 lab tubing flow meter known in the art. Fitting 69 can be similar or identical to fitting 67.

Figure 10:
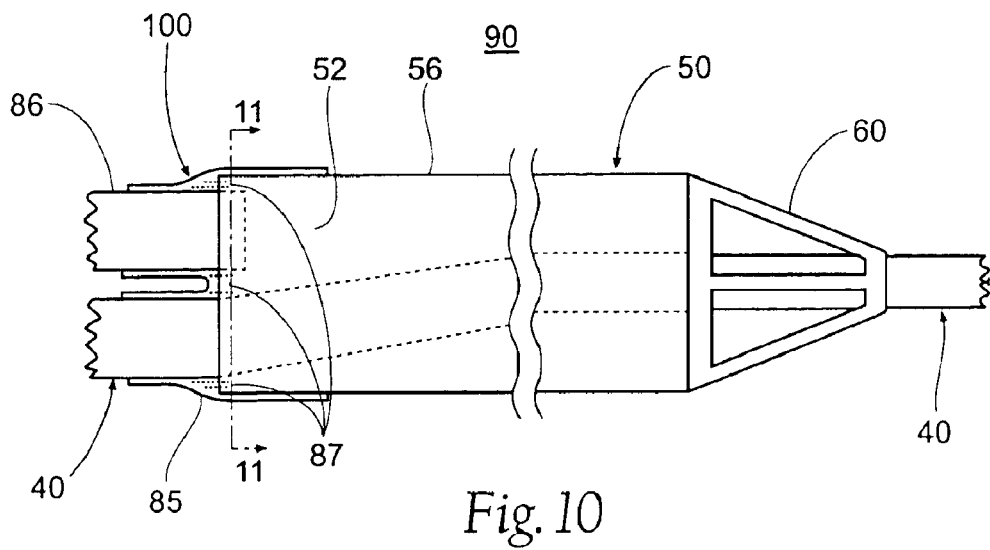
FIG. 10 is a schematic cut-away view of a parallel connector in accordance with the invention.
Figure 11:
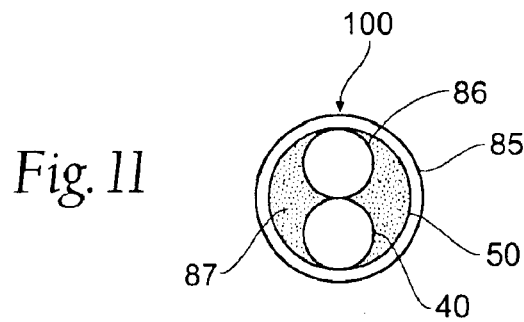
FIG. 11 is a cross-sectional view taken along line 11—11 in FIG. 10.
Figure 12:
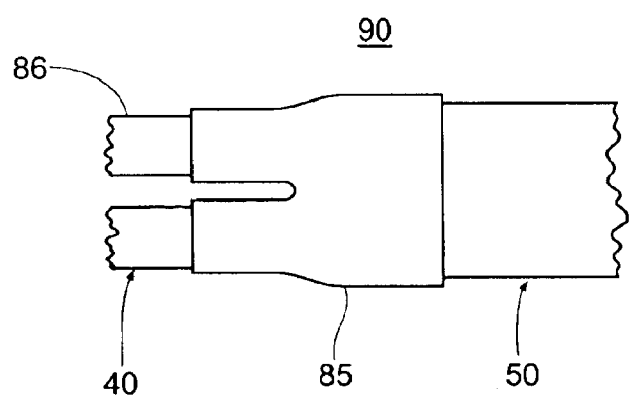
FIG. 12 is a schematic view of the parallel connector of FIG. 10.

FIGS. 10–12 show an exemplary arrangement of a second type of connector—parallel connector 100—which can be used to achieve a cannulation assembly 90 similar to cannulation assembly 30 in accordance with the invention. Specifically, outer cannula 50 is provided at its proximal end 56 with a tube 86 inserted into main lumen 52. Also inserted into main lumen 52 and adjacent tube 86 is inner cannula 40, and a suitable, bio-compatible adhesive 87 is used to retain tube 86 and cannula 40 in place in outer cannula 50. An exemplary adhesive which may be used is an ultraviolet-cured bio-compatible glue. Surrounding tube 86, inner cannula 40, outer cannula 50 and adhesive 87, at the juncture of these components, is sheathing structure 85 operating to form a fluid-tight seal. Sheathing structure 85 may for instance comprise a heat responsive material disposed over the juncture and then heated for activating and shrinking it to the appropriate size and specification.

Figure 15:
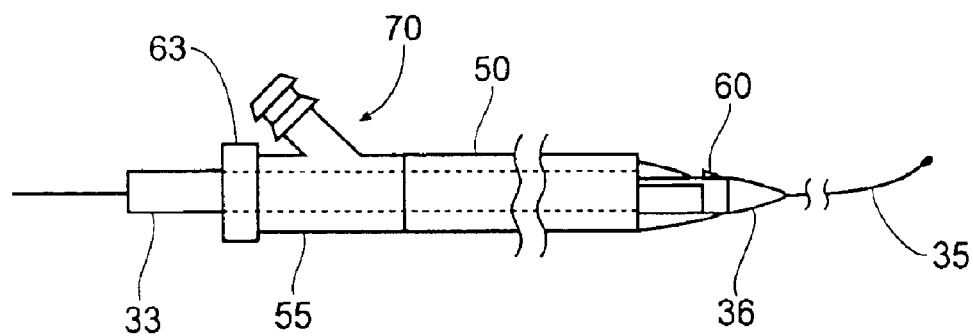
FIG. 15 is a schematic view showing a dilator in position in the outer cannula assembly.
Figure 13:
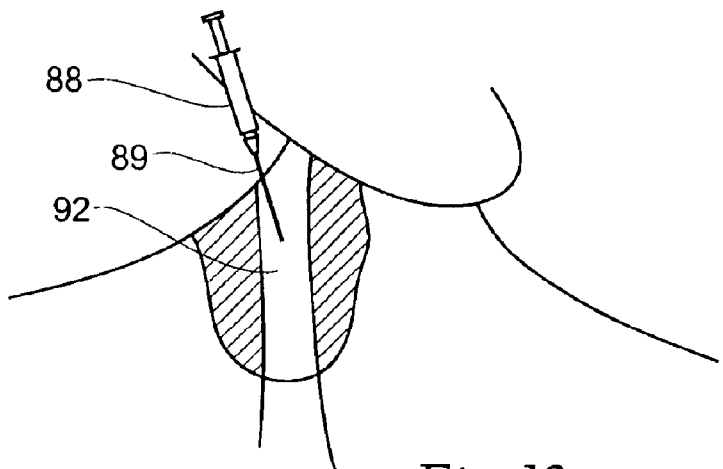
FIG. 13 is a schematic view showing the initial step of piercing the patient's vessel.
Figure 14:
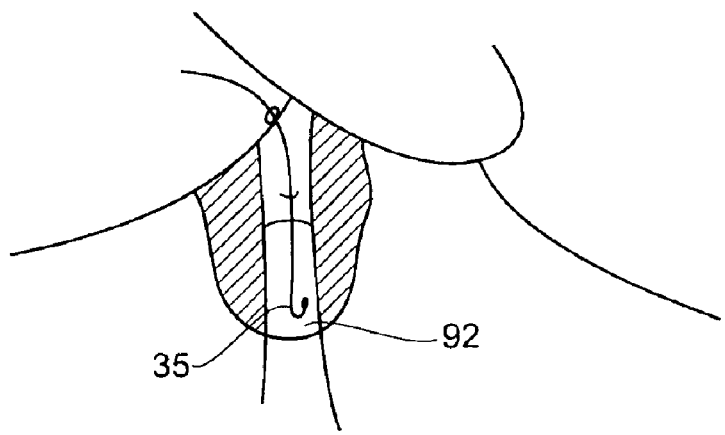
FIG. 14 is a schematic view showing the step of disposing the guide wire in the patient's vessel.
Figure 16:
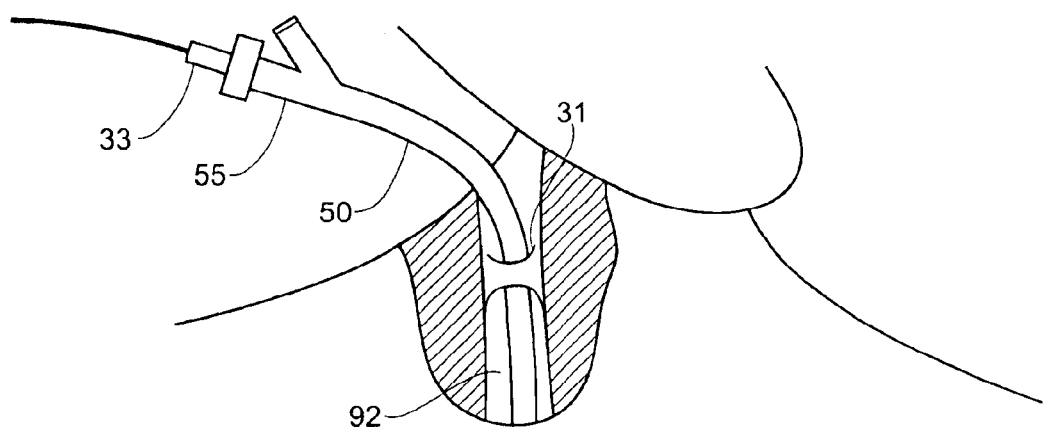
FIG. 16 is a schematic view showing the outer cannula assembly entering the patient's cardiovascular system at the brachiocephalic vein.

The surgical procedure in accordance with the invention generally follows the Seldinger technique, adapting it to the novel use for entry through the brachiocephalic (jugular) vein or carotid artery using the unique cannula arrangement herein disclosed. Accordingly, the first step of the procedure involves locating and piercing the patient's vessel using a long, hollow needle 89 attached to a syringe 88 as seen in FIG. 13. When blood enters the syringe 88, the distal end of a thin guide wire 35 is inserted through the needle 89 and into the vessel 92. The needle is then removed, leaving guide wire 35 in place in the vessel 92 (see FIG. 14). The proximal end of guide wire 35 is passed through a dilator 33, disposed axially within the outer cannula assembly 70 such that its end 36 protrudes through tip 60 as shown in FIG. 15. (At this point, outer cannula 50 does not contain inner cannula 40—that is, cannulation assembly 30 is not in the assembled configuration). Distal end 36 of dilator 33, appropriately shaped, is inserted into the vessel to thereby expand the incision, followed by outer cannula 50, which is then either partially or fully inserted into the vessel (FIG. 16). Dilator 33 is then withdrawn.

Figure 17:
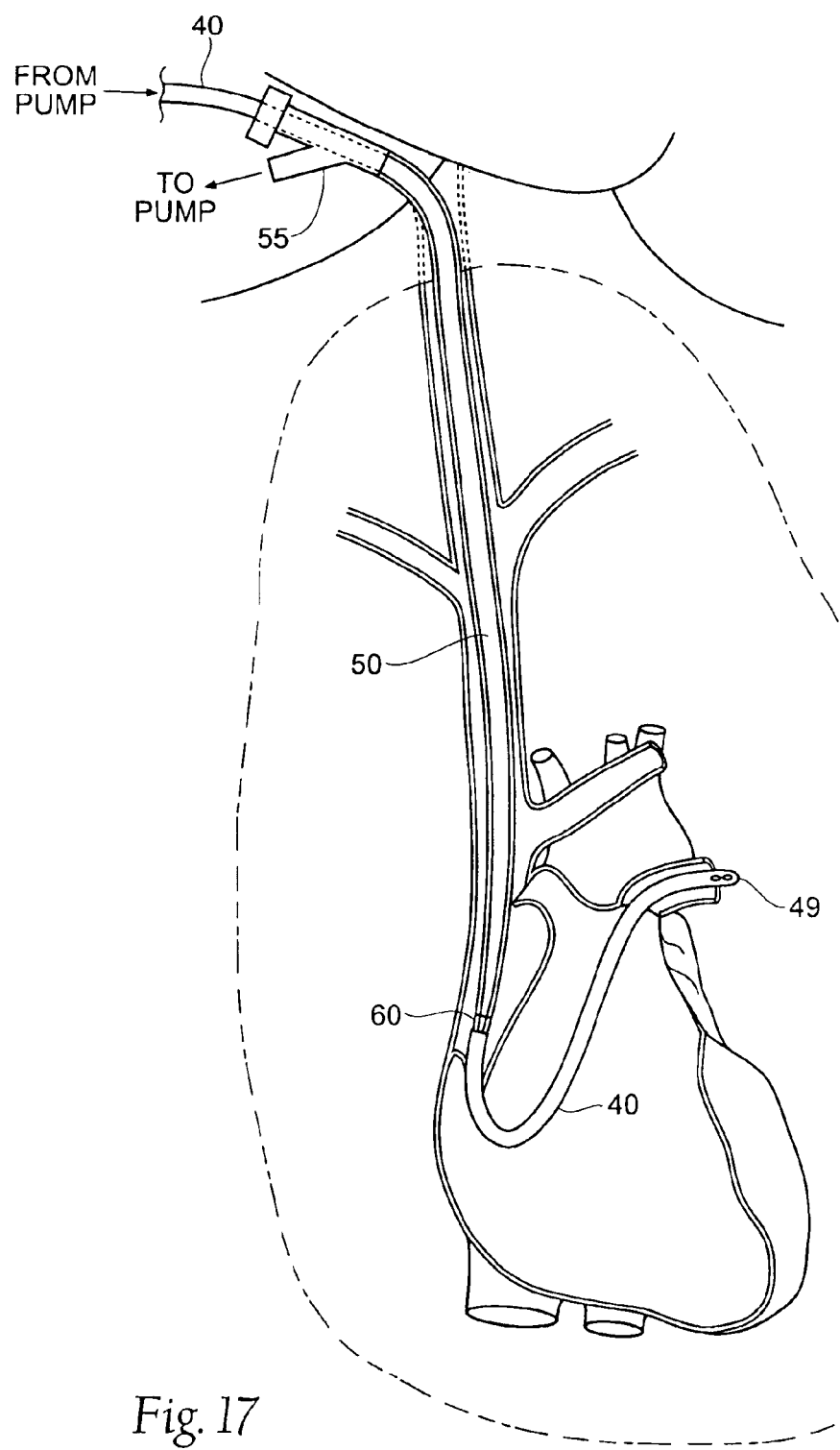
FIG. 17 is a schematic view of the cannulation assembly of the present invention in position in the patient in accordance with the present invention.

The above procedure is followed by the inner cannula insertion procedure required to achieve the assembled configuration of the cannulation assembly 30 in accordance with the invention. Inner cannula insertion can be performed using one of several options. One option involves withdrawing guide wire 35 and inserting a balloon catheter (not shown) through hemostasis valve 63. Balloon catheters are known in the art and generally comprise an inflatable balloon disposed at a distal tip of a catheter having a fluid channel for transferring inflating fluid. The balloon catheter is threaded through the outer cannula assembly 70, the brachiocephalic vein, the superior vena cava, right atrium and into the pulmonary artery. The balloon catheter is advanced into position by operation of the balloon as a "sail", whereby the balloon is inflated using the inflating fluid and powered by the natural blood flow to the destination. The balloon catheter is then used to guide the inner cannula 40 into place in the same manner as a guide wire, with the inner cannula 40 being threaded over the balloon catheter and advanced into position. With the cannulation assembly 30 thus in the assembled configuration and the inner and outer cannulas 40 and 50 in the desired bypass positions in the body as shown exemplarily in FIG. 17, the balloon catheter is withdrawn and the bypass operation commenced.

A second option for inserting inner cannula 40 into position within the patient's body is to use the guide wire 35 itself to guide the inner cannula 40 to its final destination. A particularly suitable guide wire for this would be one of the J-hook type which would facilitate negotiation of the tortuous turns involved, especially between the right atrium and pulmonary artery. Additionally, as discussed above, this negotiation is further facilitated by the one or more preformed curves 32, 34 provided at distal end 49 of inner cannula 40. Alternatively, a guidewire may be inserted into the balloon catheter to stiffen the catheter so that the cannula can be placed within the patient's body.

Alternatively, insertion in accordance with the invention may be effected utilizing the "cut down" techniques, whereby prior to insertion an incision is made in the patient's tissue, exposing the vein or artery to be accessed. The tissue and nerves surrounding the vein/artery are retracted and an incision is made in the vein/artery. After making the incision the cannula is placed within the vein/artery and advanced into the desired position. If the cannula cannot be advanced through the incision in the vein/artery, an optional dilator may be utilized to expand the diameter of the vein/artery.

Figure 30B:
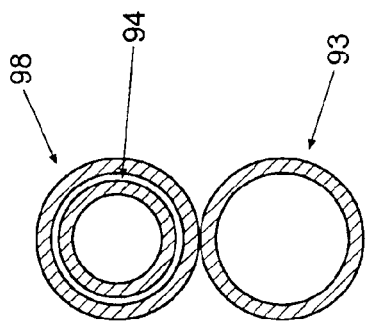
FIGS. 30A–30B are cross-sectional views taken along line 30—30 in FIG. 29 illustrating exemplary coupling mechanisms suitable for slidably coupling the first and second cannulas in accordance with the present invention.
Figure 30A:
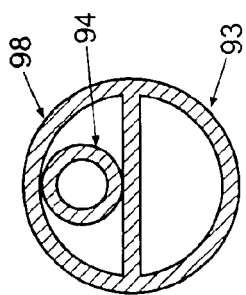
Figure 31:
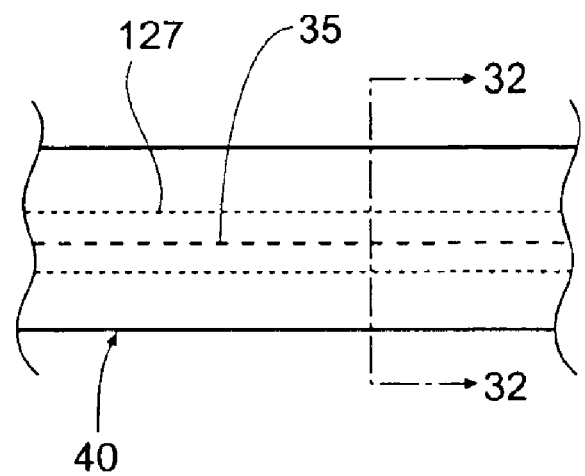
FIG. 31 is a schematic partial view showing use of auxiliary lumens in a cannula.
Figure 32:
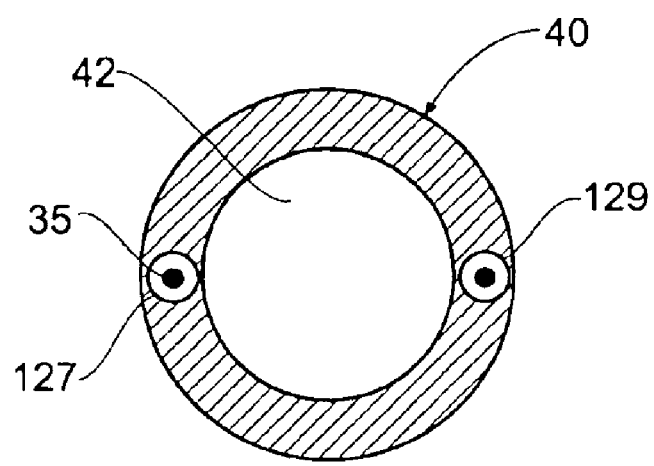
FIG. 32 is a cross-sectional view taken along line 32—32 in FIG. 31.

It is contemplated that devices such as a steerable obturator can be used to guide inner cannula 40—and, with suitable modification,.outer cannula 50—into place in the surgical site. Moreover, although during the guiding process the guiding devices such as the balloon catheter and the guide wire 35 are advanced through cannulas 40 and 50 via main lumens 42 and 52, respectively, it is also contemplated that dedicated secondary lumens 127 and 129 may be provided in the cannulas for this purpose as illustrated in FIGS. 30 and 31. Secondary lumens 127 and 129 may be formed integrally in the walls of the cannulas during the manufacturing process of the cannula, with the lumens being utilized to support the guiding device as the cannula is advanced to its destination, thus freeing up main lumens 42 and 52 for other device applications, such as equipment to monitor saturated venous oxygen (SV02), pressure and flow rate monitoring devices, etc.

Figure 18:
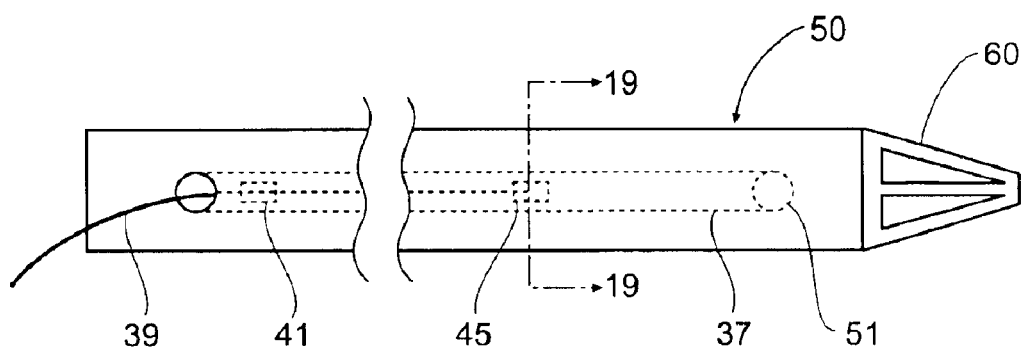
FIG. 18 is a schematic view of an outer cannula equipped with a pressure transducer in accordance with the present invention.
Figure 19:
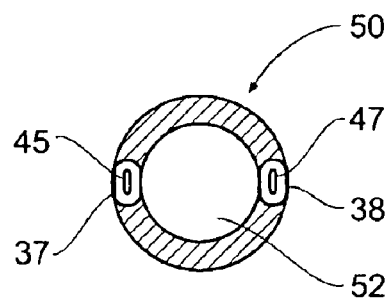
FIG. 19 is a cross-sectional view taken along line 19—19 in FIG. 18.
Figure 20:
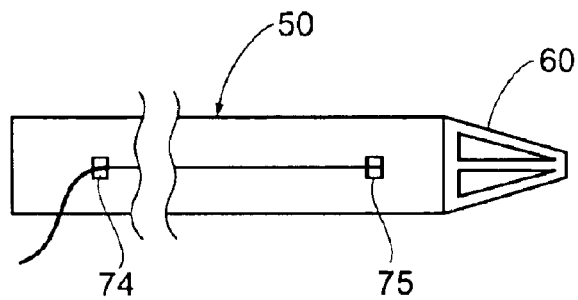
FIG. 20 is a schematic view of an outer cannula equipped with a pair of pressure transducers in accordance with the present invention.

Alternatively, as detailed below, these devices can be integrated into the cannula or supported in secondary lumens 127 and 129. For example, as shown in FIGS. 18 and 19, secondary lumens 37 and 38 can be configured for fluid communication with main lumen 52 via ports 41 and 51 and used to house therein differential pressure transducers 45, 47 and attendant wiring 39 used in the determination of fluid flow rate inside or outside cannulas 40 and 50 as described in more detail in the commonly owned and co-pending U.S. patent application Ser. No. 09/280,970 the contents of which are hereby incorporated by reference. Other types of pressure transducers can also be used and mounted in pairs (see transducers 74 and 75 of FIG. 20) integrally in the tubular wall of the cannulas in proximity to either the interior or exterior of the cannula-depending on whether an interior or exterior fluid flow rate determination is desired, thereby dispensing with the need for dedicated secondary lumens.

Figure 23:
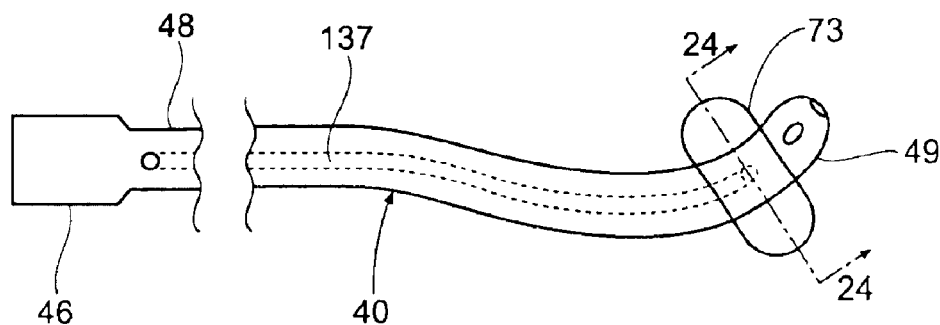
FIG. 23 is a schematic view of an inner cannula equipped with a balloon in accordance with the invention.
Figure 24:
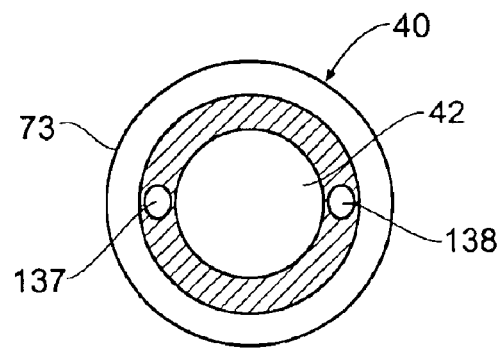
FIG. 24 is a cross-sectional view taken along line 24—24 in FIG. 23.
Figure 21:
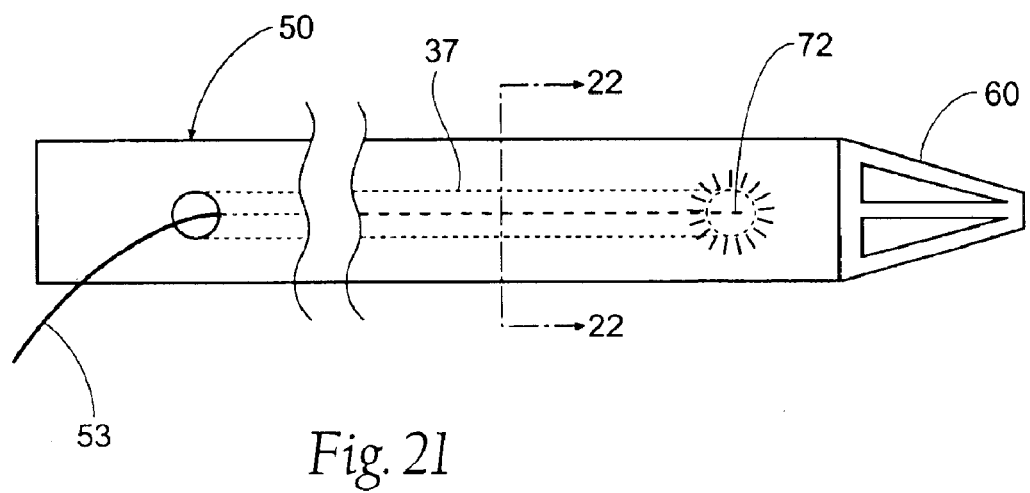
FIG. 21 is a schematic view of an outer cannula equipped with a light in accordance with the present invention.
Figure 22:
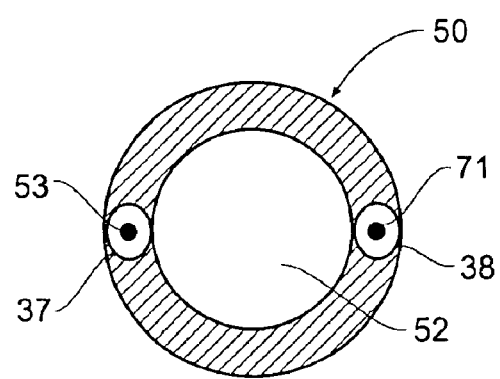
FIG. 22 is a cross-sectional view taken along line 22—22 in FIG. 21.
Figure 25:
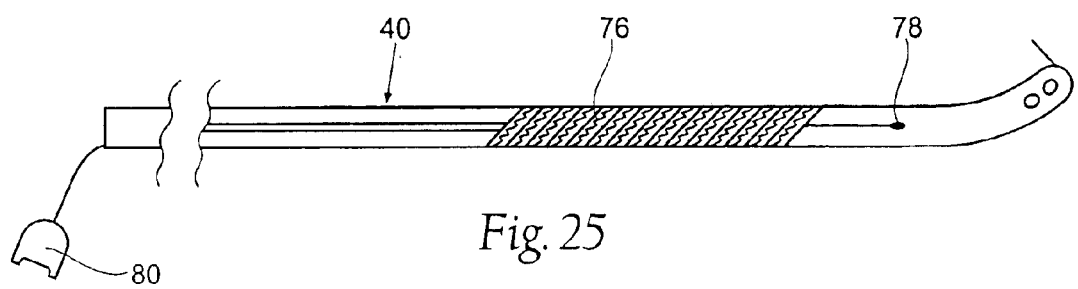
FIG. 25 is a schematic view of an inner cannula equipped with a heating-element-thermistor in accordance with the invention.
Figure 26:
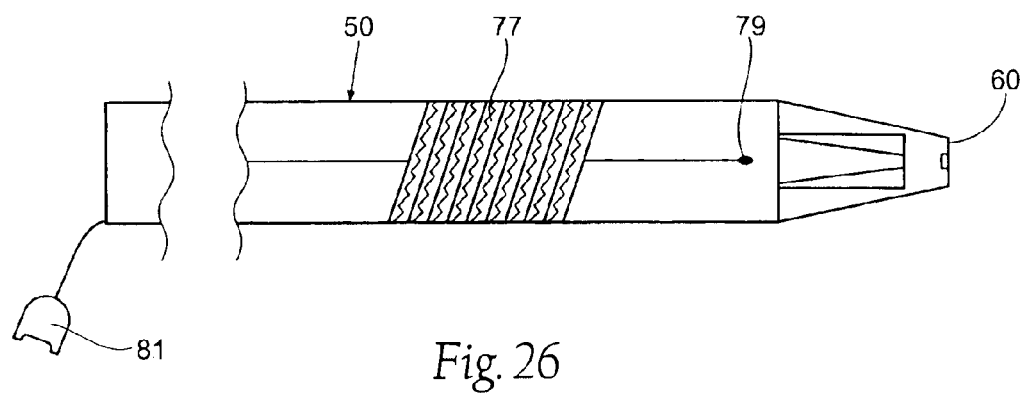
FIG. 26 is a schematic view of an outer cannula equipped with a heating-element-thermistor in accordance with the invention.

Secondary lumens are suitable to serve in a variety of surgery-facilitating fashions. For example, as shown in FIGS. 21 and 22, lumens 37 and 38 can adjustably support one or more light guides 53, 71 for projecting light, via a projecting tip 72, from the cannula to aid in its visualization as detailed in the commonly owned, co-pending U.S. patent application Ser. No. 09/280,967 (the contents of which are hereby incorporated by reference) or for optically sensing specific blood parameters such as oxygen saturation level. Similarly, lumens 137 and 138 provided in inner cannula 40 can be used for delivery of fluid to or from the distal tip 49, in order to for example dispense medication or, as shown in FIGS. 23 and 24 and detailed in the commonly owned and co-pending U.S. patent application Ser. No. 09/280,970, to inflate a balloon 73 provided at the tip of inner cannula 40 to aid in guiding the cannula to its destination during insertion without relying on separate guiding means. FIGS. 25 and 26 respectively show the use of cannulas 40 and 50 in conjunction with heating elements 76, 77 and thermistors 78, 79 disposed on a surface thereof. Thermistors 78 and 79 operate to measure fluid temperature downstream from the heating elements 76 and 77 to thereby determine fluid flow rate based on the deviation from the starting temperature as is known in the art. The measurements are relayed to appropriate processing circuits 80 and 81 for implementing the flow rate calculations. Those of ordinary skill in the art will recognize that the utility of the secondary lumens 37, 38, 137 and 138 can be extended to other applications, and the examples mentioned above are not intended to be limiting. Additionally, combinations of the above applications for the secondary lumens can be used in either or both inner cannula 40 and outer cannula 50 in accordance with the invention without inventive departure from the spirit and scope thereof.

Figure 27:
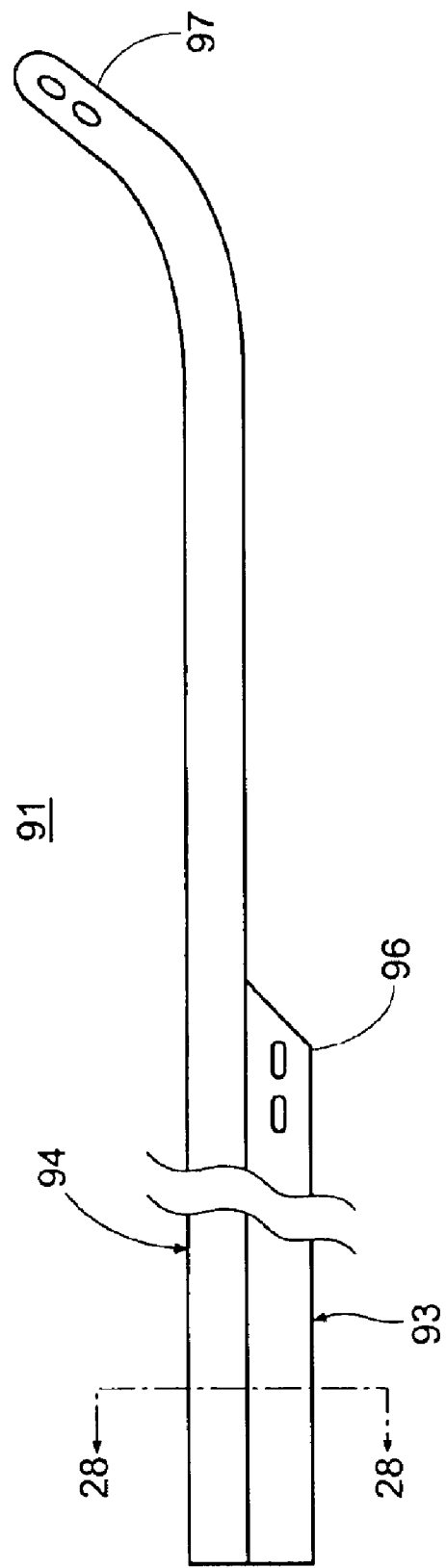
FIG. 27 is a schematic view of a cannulation assembly of the present invention having first and second cannulas disposed in a side-by-side slidable configuration according to the present invention.

FIG. 27 illustrates a cannulation assembly 91 provided in accordance with a further embodiment of the present invention. Cannulation assembly 91 includes a first cannula 93 slidably coupled to a second cannula 94. FIGS. 28A–28D illustrate a variety of exemplary coupling mechanisms 95 that can be employed to provide the slidable relation between the first cannula 93 and second cannula 94. In the embodiments shown, coupling mechanisms 95 generally comprise an elongated engagement member disposed along all or certain portions of one of the two cannulas 93, 94 capable of matingly engaging with an elongated groove or channel disposed along all or certain portions of the other cannula 93, 94.

Figure 29:
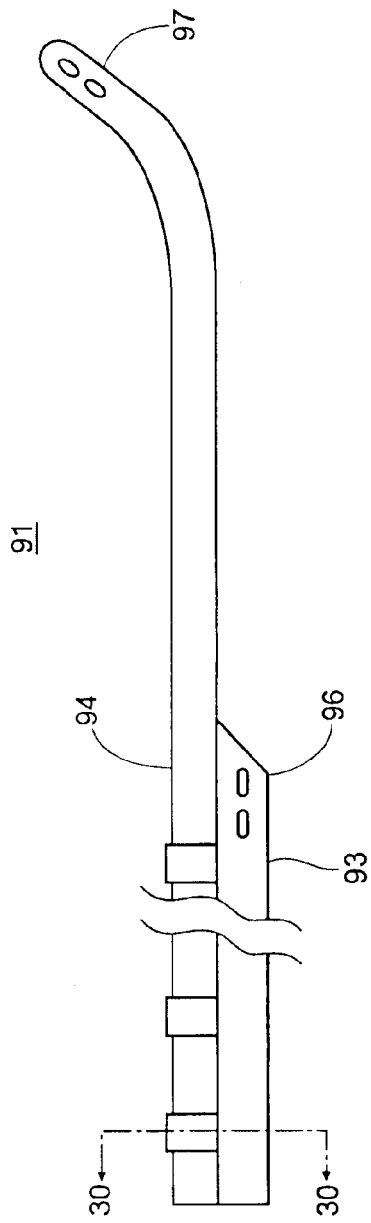
FIG. 29 is a cross-sectional view of a cannulation assembly of the present invention having first and second cannulas disposed in a second slidable side-by-side configuration according to the present invention.

In an important aspect, this allows the user great flexibility in selectively positioning the distal tip 96 of the first cannula and the distal tip 97 of the second cannula 94 within the circulatory system of a patient. For example, the slidable function of the present invention may be employed to selectively position the distal end 96 of cannula 93 in a first predetermined location and selectively position the distal end 97 of cannula 94 in a second predetermined location. Cannulation assembly 91 is introduced into the patient through an incision formed in the vascular system. This may preferably be accomplished utilizing the Seldinger technique as described above. In an exemplary embodiment, distal end 96 of first lumen 93 may be selectively advanced into the patient's atrium, thereby allowing the user to utilize the first lumen 93 as an inflow conduit. Under this same example, distal end 97 of second lumen 94 may be selectively advanced to the patient's pulmonary artery. It will be appreciate that the engagement members which form part of the coupling mechanism 95 may extend along all or portions of the respective length of the cannula 93, 94. Also, as illustrated in FIGS. 29 and 30A–30B, the slidable coupling mechanism between the individual cannulas 93, 94 may also be constructed from a barrel portion 98 fixedly attached to the first cannula 93. In so doing, the first and second cannulas 93, 94 may be selectively positioned independent of the other based on this slidable coupling.

FIGS. 33–39 illustrate several exemplary embodiments of a second main type of cannulation assembly in accordance with the present invention. A multiple lumen cannula assembly 130 in accordance with the present invention is provided comprising an inner cannula 140 slidably disposed within an outer cannula 150 having a plurality of drainage apertures 151. Outer cannula 130 may be mated with a y-connector to form outer cannula assembly 170. As noted above, the y-connector may be exchanged with any number of different connecting mechanisms without departing from the scope of the invention. Outer cannula 150 is generally cylindrical in shape having a main lumen 152 defined by a substantially tubular wall 154. Main lumen 152 extends longitudinally between the proximal end 156 to distal end 158 of outer cannula 150. The length of the cannula assembly 170 is selected depending upon the size of the patient as discussed above.

Figures 33, 34:
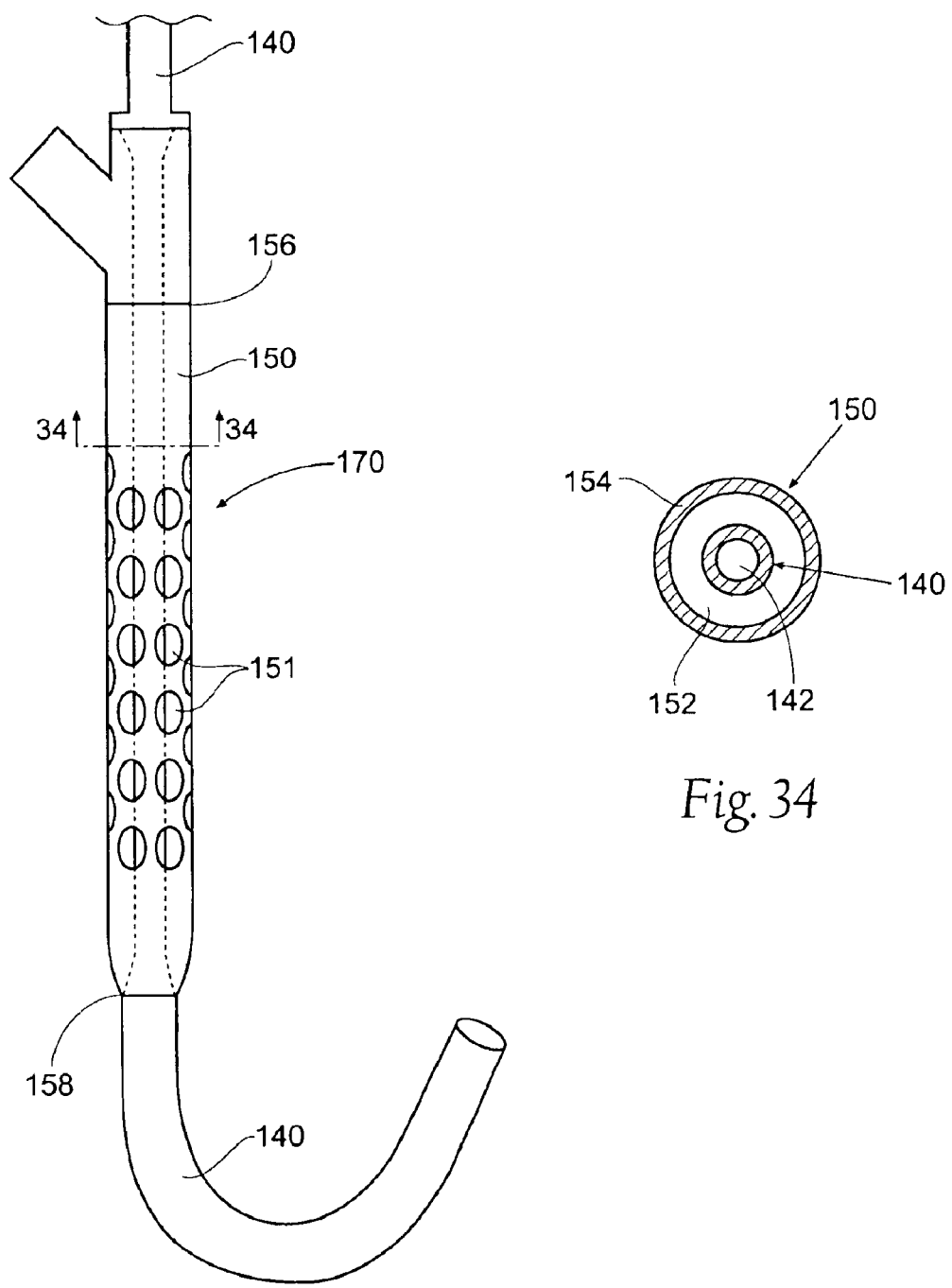
FIG. 33 is a schematic view of a cannulation assembly of the present invention having drainage apertures formed on the outer cannula and a narrow region along a length of the inner cannula.
FIG. 34 is cross-sectional view taken along line 34—34 of FIG. 33.
Figures 35, 36:
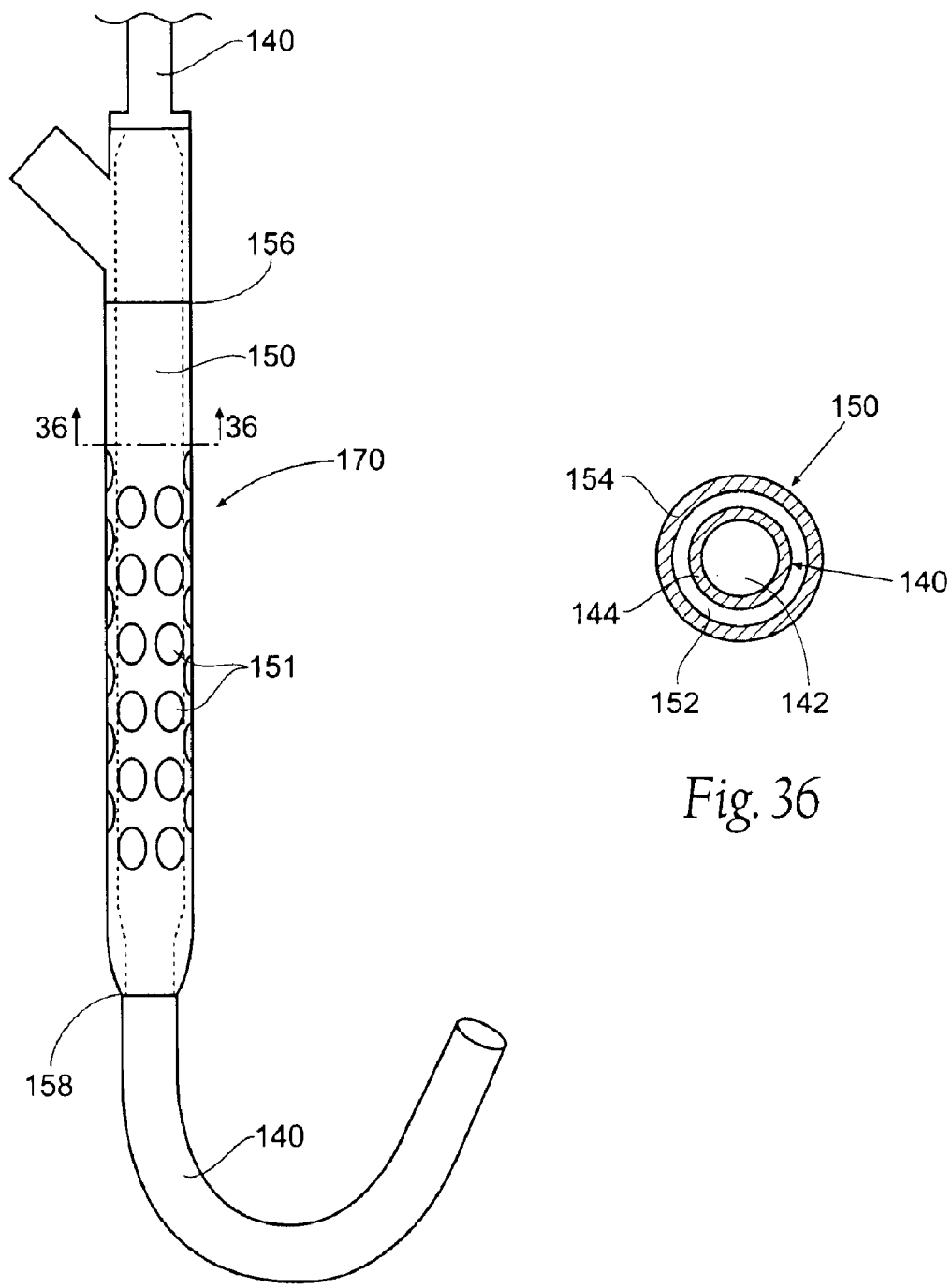
FIG. 35 is a schematic view of a cannulation assembly of the present invention having drainage apertures formed on the outer cannula and a wide region along a length of the inner cannula.
FIG. 36 is cross-sectional view taken along line 36—36 of FIG. 35.

The drainage apertures 151 of outer cannula 150 extend through wall 154 and are in fluid communication with main lumen 152. As will be appreciated, drainage apertures 151 permit the egress or ingress of fluid (depending upon the application) into or from the lumen 152 of outer cannula 150. Drainage apertures 151 may be disposed along the entire length of the outer cannula 150. In suction mode, then, blood may flow into the lumen 152 along the entire length of the outer cannula 150. This effectively decreases the distance that the blood will have to travel to reach the pumping system. It also decrease the resistance encountered by the blood being removed through the lumen 152 such that the pump will be able to pump more blood out of the outer cannula 140 at a given motor speed, thereby reducing hemolysis. FIGS. 33 and 34 illustrate alternative embodiments. FIG. 33 illustrates an embodiment wherein the inner cannula 140 includes a narrow region (shown in phantom) which, in use, extends along at least a portion of the apertures 151 formed in the outer cannula 150. FIG. 35 illustrates an embodiment wherein the inner cannula 140 includes a wide region (shown in phantom) which, in use, extends along at least a portion of the apertures 151 formed in the outer cannula 150.

Figures 37, 38:
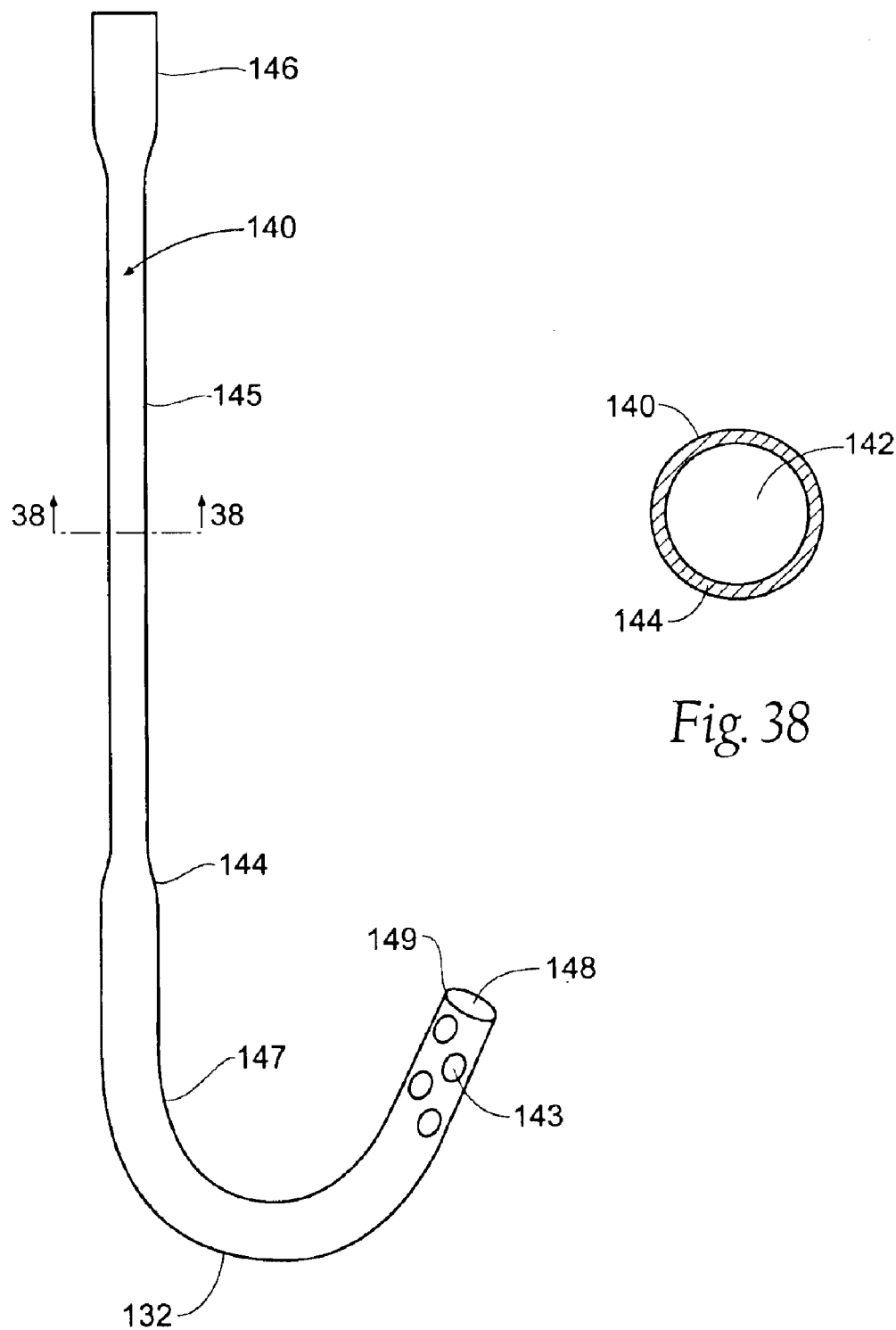
FIG. 37 is a schematic view of the inner cannula of the cannulation assembly of the type shown in FIGS. 33 and 34 having additional apertures formed near the distal tip thereof.
FIG. 38 is a cross-sectional view taken along line 38—38 of FIG. 37.

Cannula assembly 130 further comprises inner cannula 140 formed of a substantially tubular structure having a wall 144 defining a main lumen 142. The length of the cannula 140 is application specific and depends for example on the size of the patient and the distance from the incision in the neck to the destination in the patient's pulmonary system. In a CPB application, the pulmonary artery is the destination into which blood is returned into the patient from the pump system via inner cannula 140. As shown in FIG. 37, inner cannula 140 is provided at its proximal end with a connector 146, which is suitably sized to interface with various surgical instruments (not shown), including the output (or intake, in some applications) port of a reverse flow pump. Inner cannula 140 may be provided with one or more apertures 143 disposed at distal end 149, in addition to the open tip 147 of its substantially cylindrical structure, in order to permit more efficient fluid passage therethrough. Further, distal tip 149 of inner cannula 140 is bullet shaped to allow insertion into the jugular vein. Inner cannula 140 may further contain one or more preformed curves, designated as 132, to facilitate cannula maneuverability during insertion in the patient's body. The angle of the pre-formed curves may be anywhere in the range of 0–180°, with the curves being disposed anywhere along the length of the cannulas and in any one or more planes, depending upon the particular application.

Figure 39:
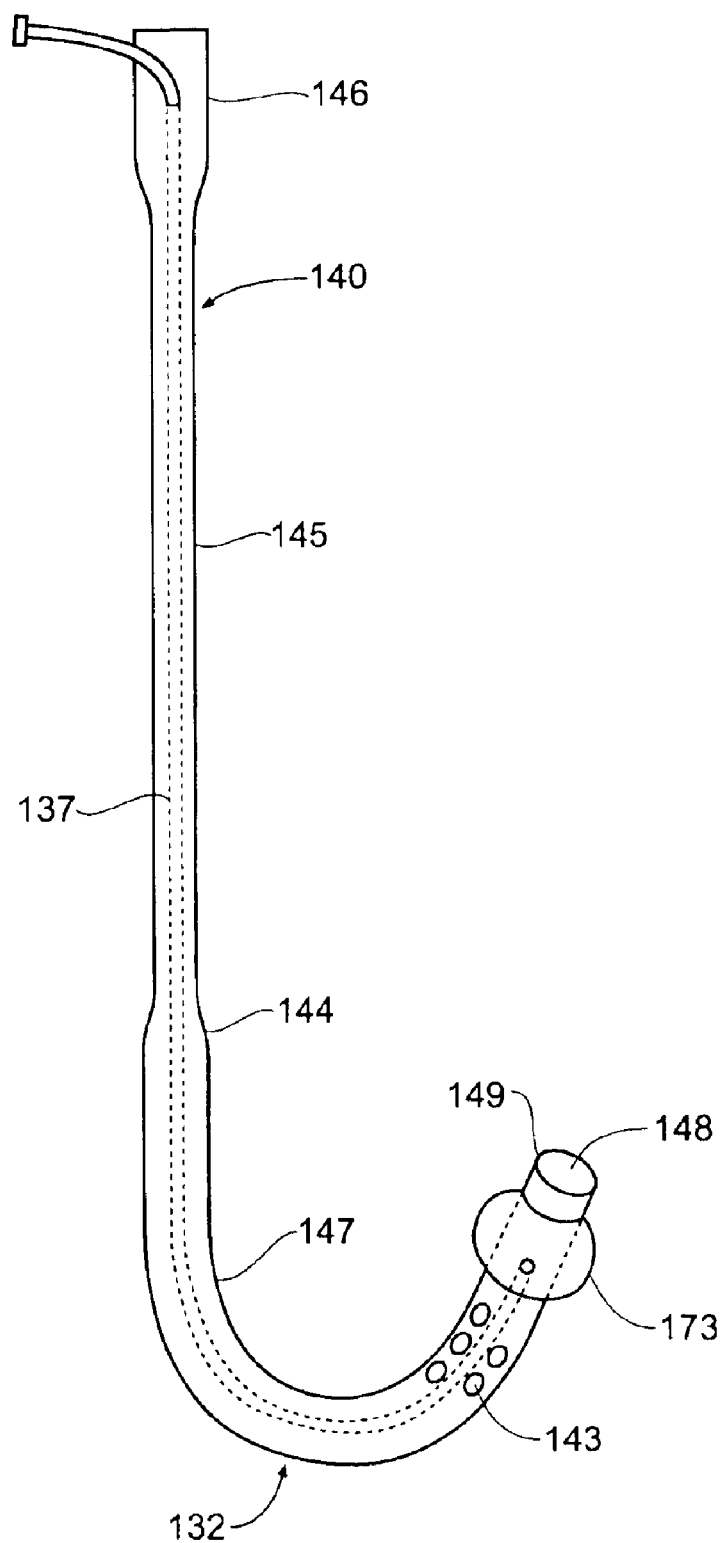
FIG. 39 is a schematic view of the inner cannula of the cannulation assembly of the type shown in FIGS. 33 and 34 further having a balloon disposed near the distal tip thereof.

As shown in FIGS. 37 and 39, inner cannula 140 may be sized to maximize flow through main lumen 142. Inner cannula 140 may be formed having varying diameter. Inner cannula 140 may also contain taper 144 adjacent to preformed section 132. The diameter of inner cannula 140 is less than the diameter distal taper 144. When inner cannula 140 is disposed within main lumen 152 of outer cannula 150, taper 144 is disposed proximal to distal end 158, or outer cannula 150. The resultant structure is an interior portion 145 disposed in outer cannula 150 and an exterior portion 148 disposed outside of outer cannula 150, with interior portion 145 having a relatively smaller outer diameter than exterior portion 148 in order to minimize obstruction of fluid flow in main lumen 152 of outer cannula 150 exterior on inner cannula 140. FIG. 39 is an illustration of an alternative embodiment of cannula 140, whereby cannula 140 further includes balloon 173 disposed radially on cannula 140 and adjacent to distal tip 149. Cannula 140 may further have drainage apertures 143 disposed proximal balloon 173. Balloon 173 may be selectively inflated/deflated through lumen 137 disposed within or upon the wall of cannula 140. The distal end of lumen 137 is in fluid communication with balloon 173. The proximal end of lumen 137 is adapted to receive medical devices such as a syringe or other inflation means.

Tubular walls of cannulas 140 and 150 can be formed of materials ranging from rigid to flexible, and in the preferred embodiments comprise semi-rigid transparent material such as polyurethane or polyvinyl chloride having a hardness between about 30A and about 90A on a Shore durometer scale and capable of sterilization by ethylene oxide (ETO). Rigid clear materials can be used for the y-connector 55, and preferably y-connector 55 is constructed of polycarbonate. The cannulas 140 and 150 may also contain radiopaque marking s (not shown) to determine placement within the patient's body. To provide structural reinforcement, a spiraling wire (not shown) can be provided to support the walls 144 and 154, and is either molded into the walls or is otherwise supported therein, and extends either partially or fully across the length of the cannulas 140 and 150. Additionally, cannulas 140 and 150 may further contain lumens (not shown) disposed within the walls as described above. Additional medical devices may be disposed within these lumens such as guidewires, catheters, blood monitoring equipment, or pressure transducers.

The advantages of the invention are many-fold. One advantage is the ability to decrease the size of the heart during surgery, thereby providing the surgeon with valuable additional space within the chest cavity. The decreased heart size is achieved by either partial or complete bypass of the heart's pumping function using the cannulas and techniques of this invention. Such bypass results in a natural decompression of the heart due to the reduced blood volume. Decompression of the heart allows a greater degree of freedom to rotate and manipulate the heart for better access to target bypass vessels. This is particularly important in endoscopic surgery.

While this invention has been described for use for right heart support, this does not limit the applications of this invention for use in right heart support only. The invention herein disclosed can be utilized in other applications apparent to those skilled in the art.

It will be appreciated by those skilled in the art that changes could be made to the embodiments described above without departing from the broad inventive concepts thereof. It is understood, therefore, that this invention is not limited to the particular embodiments disclosed, but is intended to cover modifications within the spirit and scope of the present invention as defined by the appended claims.

What is claimed is:

1. A method for providing circulatory support, comprising:

withdrawing blood from a first predetermined location in a circulatory system of a patient; and returning the withdrawn blood to a second predetermined location in the circulatory system of the patient, wherein the steps of withdrawing and returning are performed by providing a cannula assembly comprising a first cannula defining a first flow path for transporting blood between a pump and a first predetermined location within the circulatory system of a patient; and a second cannula sized and configured to slidably receive and guide at least a portion of the first cannula in a non-linear direction to extend at least a portion of the first cannula a desired length beyond the second cannula and permitting adjustment of the length the first cannula extends beyond the second cannula, the first and second cannulas forming, between them, sized and configured to slidably receive at least a portion of the first cannula to form a lumen between the first and second cannulas, the lumen defining a second flow path for transporting blood between a pump and a second predetermined location within the circulatory system of the patient, wherein the first and second cannulas are dimensioned to extend, in use, into the respective first and second predetermined locations through a single incision formed in a vascular system of patient.

2. A method for inserting a cannula assembly into a patient, comprising:

forming a single incision in the vascular system of the patient;

providing a cannula assembly comprising a first cannula defining a first flow path for transporting blood between a pump and a first predetermined location within the circulatory system of a patient; and a second cannula sized and configured to slidably receive and guide at least a portion of the first cannula in a non-linear direction to extend at least a portion of the first cannula a desired length beyond the second cannula and permitting adjustment of the length the first cannula extends beyond the second cannula, the first and second cannulas forming, between them, sized and configured to slidably receive at least a portion of the first cannula to form a lumen between the first and second cannulas, the lumen defining a second flow path for transporting blood between a pump and a second predetermined location within the circulatory system of the patient, wherein the first and second cannulas are dimensioned to extend, in use, into the respective first and second predetermined locations through a single incision formed in a vascular system of the patient;

advancing a distal end of the first cannula through the incision to a first predetermined location within the circulatory system of the patient; and advancing a distal end of the second cannula through the incision to a second predetermined location within the circulatory system of the patient.

3. A method of circulating fluid through a cannula system comprising the steps of (1) inserting the cannulation assembly into a first predetermined location in a body through a vascular incision; the assembly comprising a first cannula defining a first flow path for transporting blood between a pump and a first predetermined location within the circulatory system of a patient; and a second cannula sized and configured to slidably receive and guide at least a portion of the first cannula in a non-linear direction to extend at least a portion of the first cannula a desired length beyond the second cannula and permitting adjustment of the length the first cannula extends beyond the second cannula, the first and second cannulas forming, between them, sized and configured to slidably receive at least a portion of the first cannula to form a lumen between the first and second cannulas, the lumen defining a second flow path for transporting blood between a pump and a second predetermined location within the circulatory system of the patient wherein the first and second cannulas are dimensioned to extend, in use, into the respective first and second predetermined locations through a single incision formed in a vascular system of the patient;

(2) establishing flow communication between a first one of the flow paths and the first predetermined location;

(3) slidably moving a second one of the flow paths into a second predetermined location spaced apart from the first predetermined location;

(4) establishing flow communication between the second flow path and the second predetermined location;

(5) coupling the first and second flow paths to a pump system; and (6) operating the pump system to transport fluid from the first predetermined location for introduction into the second predetermined location.

4. A method as in claim 1 or 2 or 3 wherein the second cannula includes at least one preformed curve.

* * * * *

UNITED STATES PATENT AND TRADEMARK OFFICE
CERTIFICATE OF CORRECTION

PATENT NO. : 6,969,379 B1
DATED : November 29, 2005
INVENTOR(S) : Walid N. Aboul-Hosn and William R. Kanz It is certified that error appears in the above-identified patent and that said Letters Patent is hereby corrected as shown below:

Title page,
Item [56], References Cited, FOREIGN PATENT DOCUMENTS,
insert -- WO 01/78807   10/2001 --.
Item [57], ABSTRACT,
Line 6, after "flow" delete "path s" and substitute -- paths --.

Column 18,
Lines 19-21, after "between them," delete "sized and configured to slidably receive at least a portion of the first cannula to form".
Lines 21-22, after "a lumen" delete "between the first and second cannulas".
Lines 44-46, after "between them," delete "sized and configured to slidably receive at least a portion of the first cannula to form".
Lines 46-47, after "a lumen" delete "between the first and second cannulas".

Column 19,
Lines 10-12, after "between them", delete "sized and configured to slidably receive at least a portion of the first cannula to form".
Lines 12-13, after "a lumen" delete "between the first and second cannulas".

Signed and Sealed this

Twenty-eighth Day of February, 2006

JON W. DUDAS
*Director of the United States Patent and Trademark Office*